US009587119B2

(12) United States Patent
Hoshino et al.

(10) Patent No.: US 9,587,119 B2
(45) Date of Patent: Mar. 7, 2017

(54) FLUORINATED ETHER COMPOUND, FLUORINATED ETHER COMPOSITION, AND COATING LIQUID, AS WELL AS SUBSTRATE HAVING SURFACE LAYER, AND METHOD FOR ITS PRODUCTION

(71) Applicant: ASAHI GLASS COMPANY, LIMITED, Tokyo (JP)

(72) Inventors: Taiki Hoshino, Tokyo (JP); Nobuyuki Otozawa, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 14/862,613

(22) Filed: Sep. 23, 2015

(65) Prior Publication Data
US 2016/0009929 A1   Jan. 14, 2016

Related U.S. Application Data

(63) Continuation of application No. PCT/JP2014/059140, filed on Mar. 28, 2014.

(30) Foreign Application Priority Data

Apr. 4, 2013 (JP) ................................. 2013-078662

(51) Int. Cl.

| C09D 7/12 | (2006.01) |
|---|---|
| C08G 65/336 | (2006.01) |
| C08G 65/00 | (2006.01) |
| C09D 171/02 | (2006.01) |
| C09D 183/08 | (2006.01) |
| C09D 183/12 | (2006.01) |
| B05D 1/00 | (2006.01) |
| B05D 1/02 | (2006.01) |
| B05D 1/18 | (2006.01) |
| C07C 43/12 | (2006.01) |
| C07C 43/13 | (2006.01) |
| C07C 43/17 | (2006.01) |
| C07C 59/135 | (2006.01) |
| C07F 7/18 | (2006.01) |
| C23C 14/24 | (2006.01) |
| C08G 77/24 | (2006.01) |
| C08G 77/46 | (2006.01) |

(52) U.S. Cl.
CPC .............. *C09D 7/12* (2013.01); *B05D 1/005* (2013.01); *B05D 1/02* (2013.01); *B05D 1/18* (2013.01); *C07C 43/126* (2013.01); *C07C 43/137* (2013.01); *C07C 43/17* (2013.01); *C07C 59/135* (2013.01); *C07F 7/1836* (2013.01); *C08G 65/007* (2013.01); *C08G 65/336* (2013.01); *C09D 171/02* (2013.01); *C09D 183/08* (2013.01); *C09D 183/12* (2013.01); *C23C 14/24* (2013.01); *C08G 77/24* (2013.01); *C08G 77/46* (2013.01); *C08G 2650/48* (2013.01)

(58) Field of Classification Search
None
See application file for complete search history.

(56) References Cited

U.S. PATENT DOCUMENTS

| 3,847,978 | A | * | 11/1974 | Sianese et al. | ......... | C07C 51/60 |
| | | | | | | 524/319 |
| 5,041,588 | A | * | 8/1991 | Caporiccio | ........... | C07F 7/1832 |
| | | | | | | 556/413 |
| 5,210,253 | A | * | 5/1993 | Kinami | ................. | C07F 7/1836 |
| | | | | | | 556/448 |
| 8,211,544 | B2 | * | 7/2012 | Itami | ..................... | C07F 7/1836 |
| | | | | | | 428/429 |
| 2003/0139620 | A1 | * | 7/2003 | Yamaguchi | .......... | C08G 65/007 |
| | | | | | | 556/445 |
| 2005/0113609 | A1 | * | 5/2005 | Furukawa | ............... | C07C 43/17 |
| | | | | | | 568/685 |
| 2007/0051916 | A1 | * | 3/2007 | Flynn | .................... | C07C 43/126 |
| | | | | | | 252/71 |
| 2008/0050600 | A1 | * | 2/2008 | Fan | ........................ | C07F 7/1836 |
| | | | | | | 428/447 |

(Continued)

FOREIGN PATENT DOCUMENTS

| EP | 3081583 | 10/2016 |
|---|---|---|
| JP | 7-793 | 1/1995 |
| JP | 9-157388 | 6/1997 |
| JP | 2874715 | 3/1999 |
| JP | 2000-143991 | 5/2000 |
| JP | 2000-169481 | 6/2000 |
| JP | 2003-238577 | 8/2003 |
| JP | 2006-254400 | 9/2006 |
| JP | 2008-534696 | 8/2008 |
| JP | 2011-116947 | 6/2011 |
| WO | WO 2014/069592 | 5/2014 |

OTHER PUBLICATIONS

International Search Report issued Jul. 1, 2014 in PCT/JP2014/059140 filed Mar. 28, 2014.
Office Action issued Nov. 14, 2016, in European Patent Application No. 14778826.9.

*Primary Examiner* — Robert S Loewe
(74) *Attorney, Agent, or Firm* — Oblon, McClelland, Maier & Neustadt, L.L.P.

(57) ABSTRACT

To provide a fluorinated ether compound, a fluorinated ether composition and a coating liquid, capable of forming a surface layer which has high initial water/oil repellency and which is excellent in abrasion resistance, fingerprint stain removability, lubricity and uniformity, as well as a substrate having such a surface layer, and a method for its production. A substrate having a surface layer formed of a fluorinated ether compound represented by $D^1$-$R^{f1}$—O—$CH_2$—$(C_mF_{2m}O)_n$-A ($D^1$ is $CF_3$— or $CF_3$—O—; $R^{f1}$ is a $C_{1-20}$ fluoroalkylene group containing at least one hydrogen atom, etc.; m is 1 to 6; n is 1 to 200; A is —$C_aF_{2a}$—B—$C_bH_{2b}$—$SiL_cR_{3-c}$; B is —$C_gH_{2g}O$—, —$C_hH_{2h}O$—C(=O)NH—, etc.; L is a hydrolysable group; R is a monovalent hydrocarbon group, etc.; a is 1 to 5; b is 1 to 10; c is 1 to 3; g is 1 to 5; and h is 1 to 5) or a fluorinated ether composition containing the compound; and a method for its production.

21 Claims, No Drawings

(56) References Cited

U.S. PATENT DOCUMENTS

| | | | |
|---|---|---|---|
| 2009/0143598 A1* | 6/2009 | Herzog | C07F 7/1836 |
| | | | 548/110 |
| 2009/0208728 A1 | 8/2009 | Itami et al. | |
| 2014/0202355 A1 | 7/2014 | Hoshino | |
| 2014/0287240 A1 | 9/2014 | Murotani et al. | |
| 2014/0287246 A1 | 9/2014 | Murotani et al. | |
| 2014/0302332 A1 | 10/2014 | Murotani et al. | |
| 2014/0363682 A1* | 12/2014 | Matsuda | C07F 7/1836 |
| | | | 428/429 |
| 2016/0229875 A1* | 8/2016 | Qiu | C07F 7/1836 |

* cited by examiner

FLUORINATED ETHER COMPOUND, FLUORINATED ETHER COMPOSITION, AND COATING LIQUID, AS WELL AS SUBSTRATE HAVING SURFACE LAYER, AND METHOD FOR ITS PRODUCTION

This application is a continuation of PCT Application No. PCT/JP2014/059140, filed on Mar. 28, 2014, which is based upon and claims the benefit of priority from Japanese Patent Application No. 2013-078662 filed on Apr. 4, 2013. The contents of those applications are incorporated herein by reference in their entireties.

TECHNICAL FIELD

The present invention relates to a fluorinated ether compound, a fluorinated ether composition containing the fluorinated ether compound, or a coating liquid, which is useful for surface treatment to impart water/oil repellency to the surface of a substrate. The present invention relates to a method for producing a substrate having a surface layer by using the fluorinated ether compound, the fluorinated ether composition or the coating liquid, and the substrate having a surface layer produced by such a method.

BACKGROUND ART

A fluorinated compound is useful as a surface treating agent, since it has high lubricity, water/oil repellency, etc. By imparting water/oil repellency to a substrate surface by such a surface treating agent, stains on the substrate surface will easily be wiped off, and stain removability will be improved. Among such fluorinated compounds, a fluorinated ether compound having a poly(oxyperfluoroalkylene) chain wherein an etheric oxygen (—O—) is present in the middle of a perfluoroalkyl group, is excellent particularly in the fat and oil stain removability.

A surface treating agent containing such a fluorinated ether compound is useful for an application where a performance (abrasion resistance) such that water/oil repellency is less likely to be decreased even if repeatedly rubbed with a finger, and a performance (fingerprint stain removability) such that fingerprints attached on a surface can easily be removed by wiping, are required to be maintained for a long period of time, e.g. as a surface treating agent for a member constituting a surface to be touched with a finger, such as a touch panel.

Specifically fluorinated ether compounds of the following (1) to (3) are known as such fluorinated ether compounds.

(1) A fluorinated ether compound which has a poly(oxyperfluoroalkylene) chain and which has a perfluoroalkyl group at one terminal and has a hydrolysable silyl group at the other terminal (Patent Documents 1 and 2).

(2) A fluorinated ether compound which has a poly(oxyperfluoroalkylene) chain and which has a hydrolysable silyl group at each of both terminals (Patent Document 3).

(3) A mixture of a fluorinated ether compound which has a poly(oxyperfluoroalkylene) chain and which has a perfluoroalkyl group at one terminal and has a hydrolysable silyl group at the other terminal, and a fluorinated ether compound which has a poly(oxyperfluoroalkylene) chain and which has a hydrolysable silyl group at each of both terminals (Patent Document 4).

PRIOR ART DOCUMENTS

Patent Documents

Patent Document 1: JP-A-2000-143991
Patent Document 2: Japanese Patent No. 2,874,715
Patent Document 3: JP-A-2003-238577
Patent Document 4: JP-A-2011-116947

DISCLOSURE OF INVENTION

Technical Problem

According to findings by the present inventors, the fluorinated ether compound of (1) has a low solubility in a medium and is likely to agglomerate in a coating liquid, or even if dissolved in a medium, it is likely to agglomerate in a coating film during drying after applied on a surface of a substrate, whereby the uniformity (transparency, planarity, little irregularities) of the surface layer tends to be inadequate.

With the fluorinated ether compounds of (2) and (3), the lubricity (smoothness when the surface layer is touched by a finger) or abrasion resistance of the surface layer is inadequate.

It is an object of the present invention to provide a fluorinated ether compound, a fluorinated ether composition containing the fluorinated ether compound, and a coating liquid, capable of forming a surface layer which has high initial water/oil repellency and which is excellent in abrasion resistance, fingerprint stain removability, lubricity and uniformity.

It is an object of the present invention to provide a substrate having a surface layer which has high initial water/oil repellency and which is excellent in abrasion resistance, fingerprint stain removability, lubricity and uniformity, and a method for its production.

Solution to Problem

The present invention provides a fluorinated ether compound, a fluorinated ether composition, and a coating liquid, as well as a substrate having a surface layer, and a method for its production, which have the following constructions [1] to [15].

[1] A fluorinated ether compound represented by the following formula (1):

wherein $D^1$ is $CF_3$— or $CF_3$—O—; $R^{f1}$ is a $C_{1\text{-}20}$ fluoroalkylene group containing at least one hydrogen atom, a $C_{2\text{-}20}$ fluoroalkylene group containing at least one hydrogen atom and having an etheric oxygen atom between carbon-carbon atoms, a $C_{1\text{-}20}$ alkylene group, or a $C_{2\text{-}20}$ alkylene group having an etheric oxygen atom between carbon-carbon atoms; A is a group represented by the following formula (4); m is an integer of from 1 to 6; and n is an integer of from 1 to 200, provided that when n is 2 or more, $(C_mF_{2m}O)_n$ may be made of two or more types of $C_mF_{2m}O$ different in m;

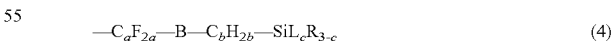

wherein B is a single bond, or —$C_gH_{2g}O$—, —$C_hH_{2h}O$—C(=O)NH— or —C(=O)—NH—; L is a hydrolysable group; R is a hydrogen atom or a monovalent hydrocarbon group; a is an integer of from 1 to 5; b is an integer of from 1 to 10; c is an integer of from 1 to 3; g is an integer of from 1 to 5; and h is an integer of from 1 to 5.

[2] The fluorinated ether compound according to [1], wherein —$CH_2$—$(C_mF_{2m}O)_n$ is —$CH_2CF_2$—O{$(CF_2O)_{n1}$ $(CF_2CF_2O)_{n2}$}(wherein n1 is an integer of at least 1, n2 is an integer of at least 1, n1+n2 is an integer of from 2 to 200, and the bond order of n1 $CF_2O$ and n2 $CF_2CF_2O$ is not limited).

[3] The fluorinated ether compound according to [1] or [2], wherein $R^{f1}$ is a group represented by the following formula (3-1), a group represented by the following formula (3-2), or a group represented by the following formula (3-3):

$$—R^F—O—CHFCF_2— \quad (3\text{-}1)$$

$$—R^F—CHFCF_2— \quad (3\text{-}2)$$

$$—R^F—C_zH_{2z}— \quad (3\text{-}3)$$

wherein $R^F$ is a single bond, a $C_{1-15}$ perfluoroalkylene group, or a $C_{2-15}$ perfluoroalkylene group having an etheric oxygen atom between carbon-carbon atoms; and z is an integer of from 1 to 4.

[4] The fluorinated ether compound according to any one of [1] to [3], which has a number average molecular weight of from 2,000 to 10,000.

[5] A fluorinated ether composition comprising the fluorinated ether compound as defined in any one of [1] to [4], and a fluorinated ether compound other than the fluorinated ether compound represented by the above formula (1).

[6] The fluorinated ether composition according to [5], wherein the content of the fluorinated ether compound represented by the above formula (1) is at least 70 mass % in the fluorinated ether composition (100 mass %).

[7] The fluorinated ether composition according to [5] or [6], wherein the fluorinated ether compound other than the fluorinated ether compound represented by the above formula (1) is a fluorinated ether compound represented by the following formula (2):

$$D^2\text{-}R^{f2}—O—CH_2—(C_pF_{2p}O)_q—C_dF_{2d}—CH_2—O—R^{f3}\text{-}D^3 \quad (2)$$

wherein each of $D^2$ and $D^3$ which are independent of each other, is $CF_3—$ or $CF_3—O—$; each of $R^{f2}$ and $R^{f3}$ which are independent of each other, is a $C_{1-20}$ fluoroalkylene group, or a $C_{2-20}$ fluoroalkylene group having an etheric oxygen atom between carbon-carbon atoms; d is an integer of from 1 to 5; p is an integer of from 1 to 6; q is an integer of from 1 to 200, provided that when q is 2 or more, $(C_pF_{2p}O)_q$ may be made of two or more types of $C_pF_{2p}O$ different in p.

[8] The fluorinated ether composition according to any one of [5] to [7], wherein the fluorinated ether compound other than the fluorinated ether compound represented by the above formula (1) is a fluorinated ether compound represented by the following formula (6):

$$R^{F1}—O—(C_sF_{2s}O)_t—R^{F2} \quad (6)$$

wherein each of $R^{F1}$ and $R^{F2}$ which are independent of each other, is a $C_{1-6}$ perfluoroalkyl group; s is an integer of from 1 to 6; and t is an integer of from 1 to 200, provided that when t is 2 or more, $(C_sF_{2s}O)_t$ may be made of two or more types of $C_sF_{2s}O$ different in s.

[9] The fluorinated ether composition according to [7] or [8], wherein the total content of the fluorinated ether compound represented by the above formula (1) and the fluorinated ether compound represented by the above formula (2) (in a case where the fluorinated ether compound represented by the above formula (6) is contained, the total content of the fluorinated ether compound represented by the formula (1), the fluorinated ether compound represented by the formula (2) and the fluorinated ether compound represented by the formula (6)) is at least 80 mass % in the fluorinated ether composition (100 mass %).

[10] A coating liquid comprising the fluorinated ether compound as defined in any one of [1] to [4] or the fluorinated ether composition as defined in any one of [5] to [9], and a medium.

[11] The coating liquid according to [10], wherein the medium is at least one organic solvent selected from the group consisting of a fluorinated alkane, a fluorinated aromatic compound and a fluoro-alkyl ether.

[12] A method for producing a substrate having a surface layer, which comprises vacuum vapor depositing the fluorinated ether compound as defined in any one of [1] to [4], or the fluorinated ether composition as defined in any one of [5] to [9], on a surface of a substrate.

[13] A method for producing a substrate having a surface layer, which comprises applying the coating liquid as defined in [10] or [11], on a surface of a substrate, followed by drying.

[14] A substrate having a surface layer which is formed of the fluorinated ether compound as defined in any one of [1] to [4], or the fluorinated ether composition as defined in any one of [5] to [9].

[15] A touch panel having, on its input surface, a substrate having a surface layer which is formed of the fluorinated ether compound as defined in any one of [1] to [4], or the fluorinated ether composition as defined in any one of [5] to [9].

Advantageous Effects of Invention

By the fluorinated ether compound, the fluorinated ether composition containing the fluorinated ether compound, and the coating liquid, of the present invention, it is possible to form a surface layer which has high initial water/oil repellency and which is excellent in abrasion resistance, fingerprint stain removability, lubricity and uniformity.

The substrate having a surface layer of the present invention has a surface layer which has high initial water/oil repellency and which is excellent in abrasion resistance, fingerprint stain removability, lubricity and uniformity.

By the method for producing a substrate having a surface layer of the present invention, it is possible to produce a substrate having a surface layer which has high initial water/oil repellency and which is excellent in abrasion resistance, fingerprint stain removability, lubricity and uniformity.

DESCRIPTION OF EMBODIMENTS

In this specification, a compound represented by the formula (1) may be referred to as compound (1). Compounds represented by other formulae may be likewise referred to.

The following definitions of terms shall apply throughout this specification and claims.

A "hydrolysable silyl group" means a group capable of forming a silanol group (Si—OH) by undergoing a hydrolytic reaction. It may, for example, be —SiL$_c$R$_{3-c}$ in the formula (4).

An "etheric oxygen atom" means an oxygen atom forming an etheric bond (—O—) between carbon-carbon atoms.

The number average molecular weight of a fluorinated ether compound is calculated by the following method using NMR analyses.

It is calculated by obtaining the number (average value) of oxyperfluoroalkylene groups based on terminal groups, by $^1$H-NMR and $^{19}$F-NMR. The terminal groups may, for example, be $R^{f1}$ or A in the formula (1).

A "fluoroalkylene group" means a group having some or all of hydrogen atoms in an alkylene group substituted by fluorine atoms, and a "perfluoroalkylene group" means a group having all of hydrogen atoms in an alkylene group substituted by fluorine atoms.

A "perfluoroalkyl group" means a group having all of hydrogen atoms in an alkyl group substituted by fluorine atoms.

A chemical formula of an oxyperfluoroalkylene group shall be presented so that the oxygen atom is shown at the right hand side of the perfluoroalkylene group.

A "surface layer" means a layer which is formed on a surface of a substrate from the fluorinated ether compound or the fluorinated ether composition of the present invention.

[Fluorinated Ether Compound Represented by the Formula (1)]

The fluorinated ether compound of the present invention is a compound (1) represented by the following formula (1).

$$D^1-R^{f1}-O-CH_2-(C_mF_{2m}O)_n-A \quad (1)$$

wherein $D^1$ is $CF_3-$ or $CF_3-O-$; $R^{f1}$ is a $C_{1-20}$ fluoroalkylene group containing at least one hydrogen atom, a $C_{2-20}$ fluoroalkylene group containing at least one hydrogen atom and having an etheric oxygen atom between carbon-carbon atoms, a $C_{1-20}$ alkylene group, or a $C_{2-20}$ alkylene group having an etheric oxygen atom between carbon-carbon atoms; A is a group represented by the following formula (4); m is an integer of from 1 to 6; and n is an integer of from 1 to 200, provided that when n is 2 or more, $(C_mF_{2m}O)_n$ may be made of two or more types of $C_mF_{2m}O$ different in m;

$$-C_aF_{2a}-B-C_bH_{2b}-SiL_cR_{3-c} \quad (4)$$

wherein B is a single bond, or $-C_gH_{2g}O-$, $-C_hH_{2h}O-C(=O)NH-$ or $-C(=O)-NH-$; L is a hydrolysable group; R is a hydrogen atom or a monovalent hydrocarbon group; a is an integer of from 1 to 5; b is an integer of from 1 to 10; c is an integer of from 1 to 3; g is an integer of from 1 to 5; and h is an integer of from 1 to 5.

(Group $D^1$)

$D^1$ has $CF_3-$ at its terminal, and therefore, one terminal of compound (1) will be $CF_3-$ and the other terminal will be a hydrolysable silyl group. By compound (1) of such a structure, it is possible to form a surface layer having a low surface energy, whereby the surface layer will be excellent in lubricity and abrasion resistance. On the other hand, by a conventional fluorinated ether compound having hydrolysable silyl groups at both terminals, the lubricity and abrasion resistance of the surface layer are inadequate.

$((C_mF_{2m}O)_n)$

With a view to sufficiently imparting abrasion resistance and fingerprint stain removability to the surface layer, m is preferably an integer of from 1 to 3, and with a view to sufficiently imparting lubricity to the surface layer, m is more preferably 1 or 2.

When m is 2 or more, $C_mF_{2m}$ may be linear or branched, but is preferably linear with a view to sufficiently imparting fingerprint stain removability and lubricity to the surface layer.

With a view to sufficiently imparting initial water/oil repellency to the surface layer, n is preferably an integer of at least 2, more preferably an integer of at least 10, particularly preferably an integer of at least 20. If the number average molecular weight of the compound (1) is too large, the number of hydrolysable silyl groups present per unit molecular weight decreases, and the abrasion resistance decreases, from such a viewpoint, n is preferably an integer of at most 150, more preferably an integer of at most 100, particularly preferably an integer of at most 80.

When n is 2 or more, $(C_mF_{2m}O)_n$ may be made of two or more types of $C_mF_{2m}O$ different in m.

In a case where two or more types of $C_mF_{2m}O$ different in m are present in $(C_mF_{2m}O)_n$, the bond order of the plural types of $C_mF_{2m}O$ is not limited. For example, in a case where $CF_2O$ and $CF_2CF_2O$ are present, $CF_2O$ and $CF_2CF_2O$ may be randomly arranged, or $CF_2O$ and $CF_2CF_2O$ may be alternately arranged. Otherwise, a block composed of a plurality of $CF_2O$ and a block composed of a plurality of $CF_2CF_2O$ may be linked.

In a case where $(C_mF_{2m}O)_n$ is made of one type of $C_mF_{2m}O$, with a view to sufficiently imparting abrasion resistance, fingerprint stain removability and lubricity to the surface layer, $(C_mF_{2m}O)_n$ is preferably $(CF_2CF_2O)_n$, $(CF_2CF_2CF_2O)_n$ or $(CF_2CF_2CF_2CF_2O)_n$, particularly preferably $(CF_2CF_2O)_n$.

With a view to sufficiently imparting abrasion resistance, fingerprint stain removability and lubricity to the surface layer, $(C_mF_{2m}O)_n$ is preferably $\{(CF_2O)_{n1}(CF_2CF_2O)_{n2}\}$ (wherein n1 is an integer of at least 1, n2 is an integer of at least 1, n1+n2 is an integer of from 2 to 200, and the bond order of n1 $CF_2O$ and n2 $CF_2CF_2O$ is not limited).

n1 is an integer of at least 1. With a view to sufficiently imparting initial water/oil repellency, abrasion resistance and fingerprint stain removability to the surface layer, n1 is preferably an integer of at least 2, more preferably an integer of at least 5, particularly preferably an integer of at least 10. From such a viewpoint that if the number average molecular weight of compound (1) is too large, the number of hydrolysable silyl groups present per unit molecular weight degreases, and the abrasion resistance decreases, n1 is preferably an integer of at most 100, more preferably an integer of at most 80, particularly preferably an integer of at most 50.

n2 is an integer of at least 1. With a view to sufficiently imparting initial water/oil repellency, abrasion resistance and fingerprint stain removability to the surface layer, n2 is preferably an integer of at least 2, more preferably an integer of at least 5, particularly preferably an integer of at least 10. From such a viewpoint that if the number average molecular weight of compound (1) is too large, the number of hydrolysable silyl groups present per unit molecular weight degreases, and the abrasion resistance decreases, n2 is preferably an integer of at most 100, more preferably an integer of at most 80, particularly preferably an integer of at most 50.

From the viewpoint of its production efficiency, compound (1) is preferably a derivative of the following fluorinated diol. The derivative of the following fluorinated diol is meant for a compound having at least one of both terminal groups $-CF_2CH_2-OH$ converted to another group. Particularly preferred is a derivative having a hydrogen atom of a hydroxy group converted to another group.

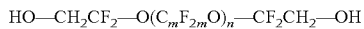

$$HO-CH_2CF_2-O(C_mF_{2m}O)_n-CF_2CH_2-OH$$

For example, in a case where $(C_mF_{2m}O)_n$ is $\{(CF_2O)_{n1}(CF_2CF_2O)_{n2}\}$, compound (1) is preferably a derivative of the following compound (10), from the viewpoint of its production efficiency.

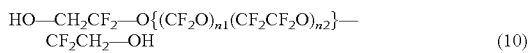

$$HO-CH_2CF_2-O\{(CF_2O)_{n1}(CF_2CF_2O)_{n2}\}-CF_2CH_2-OH \quad (10)$$

Compound (10) is a commercially available compound, or it may be synthesized from a known fluorinated polyether compound with terminal groups being $-CF_2C(O)F$, etc. by converting the terminal groups to $-CF_2CH_2OH$ by a reduction reaction, etc.

Here, in the case where compound (1) is a derivative of compound (10), —CH$_2$—(C$_m$F$_{2m}$O)$_n$— is —CH$_2$CF$_2$—O{(CF$_2$O)$_{n1}$(CF$_2$CF$_2$O)$_{n2}$}—. Further, —C$_a$F$_{2a}$— in A is —CF$_2$—, and each of g and h in B is 1.

Compound (1) has (C$_m$F$_{2m}$O)$_n$, whereby the content of fluorine atoms is large. It is thereby possible to form a surface layer which has high initial water/oil repellency and which is excellent in abrasion resistance and fingerprint stain removability.

(Group $R^{f1}$)

The number of hydrogen atoms in $R^{f1}$ is at least 1, preferably at least 2, particularly preferably at least 3, since the surface layer will thereby be excellent in uniformity. The number of hydrogen atoms in $R^{f1}$ is at most (the number of carbon atoms in $R^{f1}$)×2, preferably at most (the number of carbon atoms in $R^{f1}$) with a view to sufficiently imparting initial water/oil repellency to the surface layer.

As $R^{f1}$ has hydrogen atoms, the solubility of compound (1) in a medium tends to be high. Thus, compound (1) tends to be less likely to agglomerate in a coating liquid, and compound (1) is less likely to agglomerate in a coating film during drying after applied on the surface of a substrate, whereby the surface layer will be excellent in uniformity. On the other hand, with a conventional fluorinated ether compound wherein $R^{f1}$ does not have hydrogen atoms, the surface layer tends to be inadequate in uniformity.

From the viewpoint of the production efficiency of compound (1), $R^{f1}$ is preferably a group represented by the following formula (3-1), a group represented by the following formula (3-2), or a group represented by the following formula (3-3). Here, $R^F$ is a group to be bonded to $D^1$.

$$—R^F—O—CHFCF_2— \quad (3\text{-}1)$$

$$—R^F—CHFCF_2— \quad (3\text{-}2)$$

$$—R^F—C_zH_{2z}— \quad (3\text{-}3)$$

wherein $R^F$ is a single bond, a $C_{1-15}$ perfluoroalkylene group, or a $C_{2-15}$ perfluoroalkylene group having an etheric oxygen atom between carbon-carbon atoms, and z is an integer of from 1 to 4.

With a view to sufficiently imparting initial water/oil repellency, abrasion resistance and fingerprint stain removability to the surface layer, $R^F$ is preferably a $C_{1-9}$ perfluoroalkylene group, or a 02-13 perfluoroalkylene group having an etheric oxygen atom between carbon-carbon atoms. The perfluoroalkylene group may be linear or branched.

z is preferably an integer of from 1 to 3. When z is 3 or 4, $C_zH_{2z}$ may be linear or branched, but is preferably linear.

The following groups may be mentioned as specific examples of group $D^1$-$R^{f1}$— in a case where $R^{f1}$ is represented by the formula (3-1):

CF$_3$—O—CHFCF$_2$—
CF$_3$—CF$_2$—O—CHFCF$_2$—
CF$_3$—CF$_2$CF$_2$—O—CHFCF$_2$—
CF$_3$—CF$_2$CF$_2$CF$_2$—O—CHFCF$_2$—
CF$_3$—CF$_2$CF$_2$CF$_2$CF$_2$CF$_2$—O—CHFCF$_2$—
CF$_3$—O—CF$_2$CF$_2$—O—CHFCF$_2$—
CF$_3$—CF$_2$OCF$_2$CF$_2$—O—CHFCF$_2$—
CF$_3$—O—CF$_2$CF$_2$OCF$_2$CF$_2$—O—CHFCF$_2$—
CF$_3$—CF$_2$OCF$_2$CF$_2$OCF$_2$CF$_2$—O—CHFCF$_2$—
CF$_3$—CF$_2$CF$_2$OCF(CF$_3$)CF$_2$—O—CHFCF$_2$—
CF$_3$—CF$_2$CF$_2$OCF(CF$_3$)CF$_2$OCF(CF$_3$)CF$_2$—O—CHFCF$_2$—

The following groups may be mentioned as specific examples of group $D^1$-$R^{f1}$— in a case where $R^{f1}$ is represented by the formula (3-2):

CF$_3$—CHFCF$_2$—
CF$_3$—CF$_2$—CHFCF$_2$—
CF$_3$—CF$_2$CF$_2$—CHFCF$_2$—
CF$_3$—CF$_2$CF$_2$CF$_2$—CHFCF$_2$—

The following groups may be mentioned as specific examples of group $D^1$-$R^{f1}$— in a case where $R^{f1}$ is represented by the formula (3-3):

CF$_3$—CH$_2$—
CF$_3$—CF$_2$—CH$_2$—
CF$_3$—CF$_2$CF$_2$—CH$_2$—
CF$_3$—CF$_2$CF$_2$CF$_2$—CH$_2$—
CF$_3$—CF$_2$CF$_2$CF$_2$CF$_2$—CH$_2$—
CF$_3$—CF$_2$CF$_2$CF$_2$CF$_2$CF$_2$—CH$_2$—
CF$_3$—CF$_2$CF$_2$CF$_2$CF$_2$CF$_2$CF$_2$—CH$_2$—
CF$_3$—CH$_2$CH$_2$—
CF$_3$—CF$_2$—CH$_2$CH$_2$—
CF$_3$—CF$_2$CF$_2$—CH$_2$CH$_2$—
CF$_3$—CF$_2$CF$_2$CF$_2$—CH$_2$CH$_2$—
CF$_3$—CF$_2$CF$_2$CF$_2$CF$_2$—CH$_2$CH$_2$—
CF$_3$—CF$_2$CF$_2$CF$_2$CF$_2$CF$_2$—CH$_2$CH$_2$—
CF$_3$—CF$_2$CF$_2$CF$_2$CF$_2$CF$_2$CF$_2$—CH$_2$CH$_2$—
CF$_3$—CH$_2$CH$_2$CH$_2$—
CF$_3$—CF$_2$—CH$_2$CH$_2$CH$_2$—
CF$_3$—CF$_2$CF$_2$—CH$_2$CH$_2$CH$_2$—
CF$_3$—CF$_2$CF$_2$CF$_2$—CH$_2$CH$_2$CH$_2$—
CF$_3$—CF$_2$CF$_2$CF$_2$CF$_2$—CH$_2$CH$_2$CH$_2$—
CF$_3$—CF$_2$CF$_2$CF$_2$CF$_2$CF$_2$—CH$_2$CH$_2$CH$_2$—
CF$_3$—CF$_2$CF$_2$CF$_2$CF$_2$CF$_2$CF$_2$—CH$_2$CH$_2$CH$_2$—
CF$_3$—O—CF$_2$—CH$_2$—
CF$_3$—CF$_2$OCF$_2$—CH$_2$—
CF$_3$—O—CF$_2$CF$_2$OCF$_2$—CH$_2$—
CF$_3$—CF$_2$OCF$_2$CF$_2$OCF$_2$—CH$_2$—
CF$_3$—O—CF$_2$CF$_2$OCF$_2$CF$_2$OCF$_2$—CH$_2$—
CF$_3$—CF$_2$OCF$_2$CF$_2$OCF$_2$CF$_2$OCF$_2$—CH$_2$—

(Group A)

A is a group represented by the following formula (4).

$$—C_aF_{2a}—B—C_bH_{2b}—SiL_cR_{3-c} \quad (4)$$

wherein B is a single bond, or —C$_g$H$_{2g}$O—, —C$_h$H$_{2h}$O—C(=O)NH— or —C(=O)—NH—; L is a hydrolysable group; R is a hydrogen atom or a monovalent hydrocarbon group; a is an integer of from 1 to 5; b is an integer of from 1 to 10; c is an integer of from 1 to 3; g is an integer of from 1 to 5; and h is an integer of from 1 to 5.

L is a hydrolysable group. A hydrolysable group is a group which undergoes a hydrolytic reaction to form a hydroxy group. That is, the terminal Si-L in the compound (1) becomes a silanol group (Si—OH) by the hydrolytic reaction. The silanol group further undergoes an intermolecular reaction to form a Si—O—Si bond. Further, the silanol group undergoes a dehydration condensation reaction with a hydroxy group (substrate-OH) on the surface of a substrate to form a chemical bond (substrate-O—Si). Compound (1) has a hydrolysable silyl group at its terminal and thus is a compound which is excellent in adhesion to the substrate and further excellent in abrasion resistance, and which is capable of imparting water/oil repellency to the surface of a substrate.

L may, for example, be an alkoxy group, a halogen atom, an acyl group, an isocyanate group (—NCO), etc. The alkoxy group is preferably a $C_{1-4}$ alkoxy group. The acyl group is preferably a $C_{2-5}$ acyl group.

From the viewpoint of industrial production efficiency, L is preferably a $C_{1-4}$ alkoxy group or a halogen atom. As the halogen atom, a chlorine atom is particularly preferred. L is preferably a $C_{1-4}$ alkoxy group, since outgassing will thereby be less during coating and compound (1) will be excellent in storage stability, and in a case where storage stability of compound (1) for a long period of time is required, an ethoxy group is particularly preferred, and in a case where it is desired to shorten the reaction time after coating, a methoxy group is particularly preferred.

R is a hydrogen atom or a monovalent hydrocarbon group. The monovalent hydrocarbon group may, for example, be an alkyl group, a cycloalkyl group, an alkenyl group, an aryl group, etc.

R is preferably a monovalent hydrocarbon group, particularly preferably a monovalent saturated hydrocarbon group. The number of carbon atoms in the monovalent hydrocarbon group is preferably from 1 to 6, more preferably from 1 to 3, particularly preferably 1 or 2.

From the viewpoint of industrial production efficiency, R is preferably a $C_{1-6}$ alkyl group, more preferably a $C_{1-3}$ alkyl group, particularly preferably a $C_{1-2}$ alkyl group.

a depends on the number of m in $C_mF_{2m}O$ and is an integer of from 1 to 5. For example, in a case where the compound (1) is a derivative of the compound (10), a is 1.

b is preferably an integer of from 1 to 6, particularly preferably from 3 to 5. When b is 3 or more, $C_bH_{2b}$ may be linear or branched, but is preferably linear.

c is preferably 2 or 3, particularly preferably 3. By the presence of a plurality of L in a molecule, bonding to the surface of a substrate becomes stronger.

When c is 2 or more, the plurality of L present in one molecule may be the same or different from one another. They are preferably the same, from the viewpoint of easy availability or easy production of the raw material.

g is preferably an integer of from 1 to 3, and when g is 3 or more, $C_gH_{2g}$ may be linear or branched, but is preferably linear.

h is preferably an integer of from 1 to 3, and when h is 3 or more, $C_hH_{2h}$ may be linear or branched, but is preferably linear.

Here, in a case where compound (1) is a derivative of compound (10), each of g and h is 1.

—$SiL_cR_{3-c}$ is preferably —$Si(OCH_3)_3$, —$SiCH_3(OCH_3)_2$, —$Si(OCH_2CH_3)_3$, —$SiCl_3$, —$Si(OCOCH_3)_3$ or —$Si(NCO)_3$. From the viewpoint of handling efficiency in the industrial production, —$Si(OCH_3)_3$ is particularly preferred.

(Preferred Embodiments of Compound (1))

Compound (1) is preferably a compound having the above-mentioned preferred group $D^1$-$R^{f1}$, preferred $(C_mF_{2m}O)_n$ and preferred group A combined. Particularly preferred are compounds represented by the following formulae (111), (112), (113), (121), (122), (123), (131), (132) and (133). Compounds (111), (112), (113), (121), (122), (123), (131), (132) and (133) are derivatives of compound (10), and therefore, they are easy to produce on an industrial scale, easy to handle and capable of sufficiently imparting initial water/oil repellency, abrasion resistance, fingerprint stain removability, lubricity and uniformity to the surface layer.

$$D^1\text{-}R^F\text{—}O\text{—}CHFCF_2\text{—}O\text{—}CH_2CF_2\text{—}O\{(CF_2O)_{n1}(CF_2CF_2O)_{n2}\}\text{—}CF_2CH_2\text{—}O\text{—}C_bH_{2b}\text{—}SiL_cR_{3-c} \quad (111)$$

$$D^1\text{-}R^F\text{—}O\text{—}CHFCF_2\text{—}O\text{—}CH_2CF_2\text{—}O\{(CF_2O)_{n1}(CF_2CF_2O)_{n2}\}\text{—}CF_2CH_2\text{—}O\text{—}C(=O)NH\text{—}C_bH_{2b}\text{—}SiL_cR_{3-c} \quad (112)$$

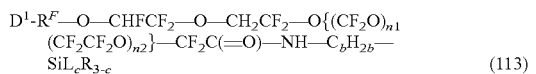

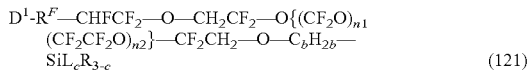

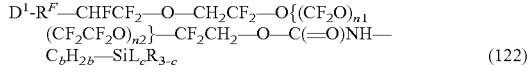

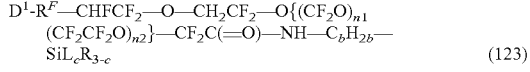

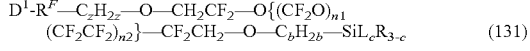

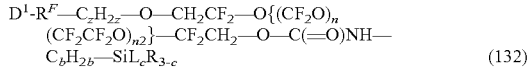

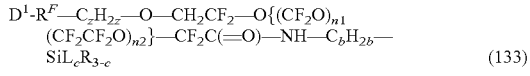

(Method for Producing Compound (1))
Method for Producing Compound (111):
<Method i> When b is 3 or more, compound (111) may be produced as follows.

In the presence of a basic compound, compound (10) is reacted with $D^1$-$R^F$—O—CF=$CF_2$ to obtain a mixture of compound (11), compound (21) and unreacted compound (10).

$$HO\text{—}CH_2CF_2\text{—}O\{(CF_2O)_{n1}(CF_2CF_2O)_{n2}\}\text{—}CF_2CH_2\text{—}OH \quad (10)$$

$$D^1\text{-}R^F\text{—}O\text{—}CHFCF_2\text{—}O\text{—}CH_2CF_2\text{—}O\{(CF_2O)_{n1}(CF_2CF_2O)_{n2}\}\text{—}CF_2CH_2\text{—}OH \quad (11)$$

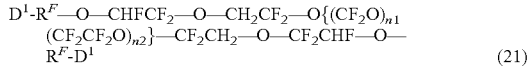

From the mixture, compound (11) is isolated, and in the presence of a basic compound, compound (11) is reacted with X—$C_{b-2}H_{2(b-2)}$—CH=$CH_2$ to obtain compound (12). X is a leaving group such as I, Br or Cl.

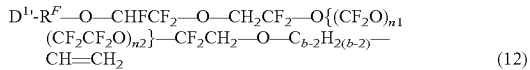

Compound (12) and $HSiL_cR_{3-c}$ are subjected to a hydrosilylation reaction to obtain compound (111a), or a mixture of compound (111a) and compound (111b). The hydrosilylation reaction is preferably conducted by using a transition metal catalyst such as platinum, or a radical generating agent such as an organic peroxide.

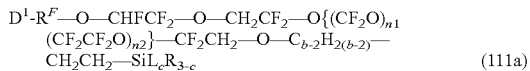

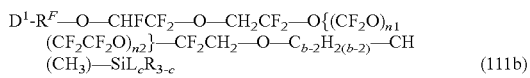

<Method ii> When b is at least 1, compound (111) may be produced as follows.

In the presence of a basic compound, compound (11) is reacted with X—$C_bH_{2b}$—$SiL_cR_{3-c}$ to obtain compound (111). X is a leaving group such as I, Br or Cl.

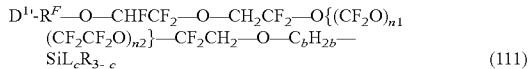

Method for Producing Compound (112):
Compound (112) may be produced as follows.

In the presence of a urethanization catalyst, compound (11) is reacted with OCN—$C_bH_{2b}$—$SiL_cR_{3-c}$ to obtain compound (112).

$$D^1\text{-}R^F\text{—O—CHFCF}_2\text{—O—CH}_2\text{CF}_2\text{—O}\{(CF_2O)_{n1}(CF_2CF_2O)_{n2}\}\text{—CF}_2CH_2\text{—O—C(=O)NH—}C_bH_{2b}\text{—SiL}_cR_{3-c} \quad (112)$$

Method for Producing Compound (113):

Compound (113) may be produced as follows.

Compound (11) is oxidized to obtain compound (13a). In some cases, compound (13a) may be esterified to obtain compound (13b). $R^1$ is an alkyl group.

$$D^1\text{-}R^F\text{—O—CHFCF}_2\text{—O—CH}_2CF_2\text{—O}\{(CF_2O)_{n1}(CF_2CF_2O)_{n2}\}\text{—CF}_2C(=O)OH \quad (13a)$$

$$D^1\text{-}R^F\text{—O—CHFCF}_2\text{—O—CH}_2CF_2\text{—O}\{(CF_2O)_{n1}(CF_2CF_2O)_{n2}\}\text{—CF}_2C(=O)OR^1 \quad (13b)$$

Compound (13a) or compound (13b) is reacted with $H_2N$—$C_bH_{2b}$—$SiL_cR_{3-c}$ to obtain compound (113).

$$D^1\text{-}R^F\text{—O—CHFCF}_2\text{—O—CH}_2CF_2\text{—O}\{(CF_2O)_{n1}(CF_2CF_2O)_{n2}\}\text{—CF}_2C(=O)\text{—NH—}C_bH_{2b}\text{—SiL}_cR_{3-c} \quad (113)$$

Method for Producing Compound (121):

<Method i> When b is 3 or more, compound (121) may be produced as follows.

In the presence of a basic compound, compound (10) is reacted with $D^1\text{-}R^F$—$CF=CF_2$ to obtain a mixture of compound (14), compound (22) and unreacted compound (10).

$$HO\text{—}CH_2CF_2\text{—O}\{(CF_2O)_{n1}(CF_2CF_2O)_{n2}\}\text{—}CF_2CH_2\text{—OH} \quad (10)$$

$$D^1\text{-}R^F\text{—CHFCF}_2\text{—O—CH}_2CF_2\text{—O}\{(CF_2O)_{n1}(CF_2CF_2O)_{n2}\}\text{—CF}_2CH_2\text{—OH} \quad (14)$$

$$D^1\text{-}R^F\text{—CHFCF}_2\text{—O—CH}_2CF_2\text{—O}\{(CF_2O)_{n1}(CF_2CF_2O)_{n2}\}\text{—CF}_2CH_2\text{—O—CF}_2CHF\text{—}R^F\text{-}D^1 \quad (22)$$

From the mixture, compound (14) is isolated, and in the presence of a basic compound, compound (14) is reacted with X—$C_{b-2}H_{2(b-2)}$—$CH=CH_2$ to obtain compound (15). X is a leaving group such as I, Br or Cl.

$$D^1\text{-}R^F\text{—CHFCF}_2\text{—O—CH}_2CF_2\text{—O}\{(CF_2O)_{n1}(CF_2CF_2O)_{n2}\}\text{—CF}_2CH_2\text{—O—}C_{b-2}H_{2(b-2)}\text{—}CH=CH_2 \quad (15)$$

Compound (15) and $HSiL_cR_{3-c}$ are subjected to a hydrosilylation reaction to obtain compound (121a), or a mixture of compound (121a) and compound (121b). The hydrosilylation reaction is preferably conducted by using a transition metal catalyst such as platinum, or a radical generating agent such as an organic peroxide.

$$D^1\text{-}R^F\text{—CHFCF}_2\text{—O—CH}_2CF_2\text{—O}\{(CF_2O)_{n1}(CF_2CF_2O)_{n2}\}\text{—CF}_2CH_2\text{—O—}C_{b-2}H_{2(b-2)}\text{—}CH_2CH_2\text{—SiL}_cR_{3-c} \quad (121a)$$

$$D^1\text{-}R^F\text{—CHFCF}_2\text{—O—CH}_2CF_2\text{—O}\{(CF_2O)_{n1}(CF_2CF_2O)_{n2}\}\text{—CF}_2CH_2\text{—O—}C_{b-2}H_{2(b-2)}\text{—CH}(CH_3)\text{—SiL}_cR_{3-c} \quad (121b)$$

<Method ii> When b is at least 1, compound (121) may be produced as follows.

In the presence of a basic compound, compound (14) is reacted with X—$C_bH_{2b}$—$SiL_cR_{3-c}$ to obtain compound (121). X is a leaving group such as I, Br or Cl.

$$D^1\text{-}R^F\text{—CHFCF}_2\text{—O—CH}_2CF_2\text{—O}\{(CF_2O)_{n1}(CF_2CF_2O)_{n2}\}\text{—CF}_2CH_2\text{—O—}C_bH_{2b}\text{—SiL}_cR_{3-c} \quad (121)$$

Method for Producing Compound (122):

Compound (122) may be produced as follows.

In the presence of a urethanization catalyst, compound (14) is reacted with OCN—$C_bH_{2b}$—$SiL_cR_{3-c}$ to obtain compound (122).

$$D^1\text{-}R^F\text{—CHFCF}_2\text{—O—CH}_2CF_2\text{—O}\{(CF_2O)_{n1}(CF_2CF_2O)_{n2}\}\text{—CF}_2CH_2\text{—O—C(=O)NH—}C_bH_{2b}\text{—SiL}_cR_{3-c} \quad (122)$$

Method for Producing Compound (123):

Compound (123) may be produced as follows.

Compound (14) is oxidized to obtain compound (16a). In some cases, compound (16a) may be esterified to obtain compound (16b). $R^1$ is an alkyl group.

$$D^1\text{-}R^F\text{—CHFCF}_2\text{—O—CH}_2CF_2\text{—O}\{(CF_2O)_{n1}(CF_2CF_2O)_{n2}\}\text{—CF}_2C(=O)OH \quad (16a)$$

$$D^1\text{-}R^F\text{—CHFCF}_2\text{—O—CH}_2CF_2\text{—O}\{(CF_2)_{n1}(CF_2CF_2O)_{n2}\}\text{—CF}_2C(=O)OR^1 \quad (16b)$$

Compound (16a) or compound (16b) is reacted with $H_2N$—$C_bH_{2b}$—$SiLR_{3-c}$ to obtain compound (123).

$$D^1\text{-}R^F\text{—CHFCF}_2\text{—O—CH}_2CF_2\text{—O}\{(CF_2O)_{n1}(CF_2CF_2O)_{n2}\}\text{—CF}_2C(=O)\text{—NH—}C_bH_{2b}\text{—SiL}_cR_{3-c} \quad (123)$$

Method for Producing Compound (131):

<Method i> When b is 3 or more, compound (131) may be produced as follows.

In the presence of a basic compound, compound (10) is reacted with $D^1\text{-}R^F$—$C_zH_{2z}$—Z to obtain a mixture of compound (17), compound (23) and unreacted compound (10). Z is a leaving group, such as I, Br, Cl, OC(=O)CF$_3$, OSO$_2$CH$_3$ or OSO$_2$Ph (Ph is a phenyl group).

$$HO\text{—}CH_2CF_2\text{—O}\{(CF_2O)_{n1}(CF_2CF_2O)_{n2}\}\text{—}CF_2CH_2\text{—OH} \quad (10)$$

$$D^1\text{-}R^F\text{—}C_zH_{2z}\text{—O—CH}_2CF_2\text{—O}\{(CF_2O)_{n1}(CF_2CF_2O)_{n2}\}\text{—CF}_2CH_2\text{—OH} \quad (17)$$

$$D^1\text{-}R^F\text{—}C_zH_{2z}\text{—O—CH}_2CF_2\text{—O}\{(CF_2O)_{n1}(CF_2CF_2O)_{n2}\}\text{—CF}_2CH_2\text{—O—}C_zH_{2z}\text{—}R^F\text{-}D^1 \quad (23)$$

From the mixture, compound (17) is isolated, and in the presence of a basic compound, compound (17) is reacted with X—$C_{b-2}H_{2(b-2)}$—$CH=CH_2$ to obtain compound (18). X is a leaving group such as I, Br or Cl.

$$D^1\text{-}R^F\text{—}C_zH_{2z}\text{—O—CH}_2CF_2\text{—O}\{(CF_2O)_{n1}(CF_2CF_2O)_{n2}\}\text{—CF}_2CH_2\text{—O—}C_{b-2}H_{2(b-2)}\text{—}CH=CH_2 \quad (18)$$

Compound (18) and $HSiL_cR_{3-c}$ are subjected to a hydrosilylation reaction to obtain compound (131a), or a mixture of compound (131a) and compound (131b). The hydrosilylation reaction is preferably conducted by using a transition metal catalyst such as platinum, or a radical generating agent such as an organic peroxide.

$$D^1\text{-}R^F\text{—}C_zH_{2z}\text{—O—CH}_2CF_2\text{—O}\{(CF_2O)_{n1}(CF_2CF_2O)_{n2}\}\text{—CF}_2CH_2\text{—O—}C_{b-2}H_{2(b-2)}\text{—}CH_2CH_2\text{—SiL}_cR_{3-c} \quad (131a)$$

$$D^1\text{-}R^F\text{—}C_zH_{2z}\text{—O—CH}_2CF_2\text{—O}\{(CF_2O)_{n1}(CF_2CF_2O)_{n2}\}\text{—CF}_2CH_2\text{—O—}C_{b-2}H_{2(b-2)}\text{—CH}(CH_3)\text{—SiL}_cR_{3-c} \quad (131b)$$

<Method ii> When b is at least 1, compound (131) may be produced as follows.

In the presence of a basic compound, compound (17) is reacted with X—$C_bH_{2b}$—$SiL_cR_{3-c}$ to obtain compound (131). X is a leaving group such as I, Br or Cl.

$$D^1\text{-}R^F\text{—}C_zH_{2z}\text{—O—CH}_2CF_2\text{—O}\{(CF_2O)_{n1}(CF_2CF_2O)_{n2}\}\text{—CF}_2CH_2\text{—O—}C_bH_{2b}\text{—SiLR}_{3-c} \quad (131)$$

Method for Producing Compound (132):

Compound (132) may be produced as follows.

In the presence of a urethanization catalyst, compound (17) is reacted with OCN—$C_bH_{2b}$—$SiL_cR_{3-c}$ to obtain compound (132).

$$D^1\text{-}R^F\text{—}C_zH_{2z}\text{—}O\text{—}CH_2CF_2\text{—}O\{(CF_2O)_{n1}$$
$$(CF_2CF_2O)_{n2}\}\text{—}CF_2CH_2\text{—}O\text{—}C(\!\!=\!\!O)NH\text{—}$$
$$C_bH_{2b}\text{—}SiL_cR_{3\text{-}c} \qquad (132)$$

Method for Producing Compound (133):

Compound (133) may be produced as follows.

Compound (17) is oxidized to obtain compound (19a). In some cases, compound (19a) may be esterified to obtain compound (19b). $R^1$ is an alkyl group, etc.

$$D^1\text{-}R^F\text{—}C_zH_{2z}\text{—}O\text{—}CH_2CF_2\text{—}O\{(CF_2O)_{n1}$$
$$(CF_2CF_2O)_{n2}\}\text{—}CF_2C(\!\!=\!\!O)OH \qquad (19a)$$

$$D^1\text{-}R^F\text{—}C_zH_{2z}\text{—}O\text{—}CH_2CF_2\text{—}O\{(CF_2O)_{n1}$$
$$(CF_2CF_2O)_{n2}\}\text{—}CF_2C(\!\!=\!\!O)OR^1 \qquad (19b)$$

Compound (19a) or compound (19b) is reacted with $H_2N\text{—}C_bH_{2b}\text{—}SiL_cR_{3\text{-}c}$ to obtain compound (133).

$$D^1\text{-}R^F\text{—}C_zH_{2z}\text{—}O\text{—}CH_2CF_2\text{—}O\{(CF_2O)_{n1}$$
$$(CF_2CF_2O)_{n2}\}\text{—}CF_2C(\!\!=\!\!O)\text{—}NH\text{—}C_bH_{2b}\text{—}$$
$$SiL_cR_{3\text{-}c} \qquad (133)$$

According to the foregoing method for producing compound (1), it is possible to simply obtain any desired compound (1) by the addition reaction or substitution reaction under mild conditions using commercially available compound (10) as raw material.

Further, compound (11), compound (14) or compound (17) as an intermediate to obtain compound (1) is an alcohol having a proper polarity at its terminal, and therefore, it can easily be isolated by a common column purification using silica gel. Therefore, desired compound (11), compound (14) or compound (17) can be isolated from a mixture of compound (11), compound (21) and unreacted compound (10), a mixture of compound (14), compound (22) and unreacted compound (10), or a mixture of compound (17), compound (23) and unreacted compound (10), so that unreacted compound (10) will not remain in such compound, or even if it remains, its amount is little. Accordingly, a fluorinated ether compound having hydrolysable silyl groups at both terminals, obtainable from unreacted compound (10), will not be contained in finally obtainable compound (1), or even if contained, the content is little. Further, by isolating compound (21), compound (22) or compound (23), being compound (2), it is possible to effectively utilize compound (2) as one component to be added to the after-described fluorinated ether composition.

Compound (1) of the present invention may be a single compound composed of one type of compound (1), or may be a mixture composed of two or more types of compound (1) different in $D^1$, $R^{f1}$, $(C_mF_{2m}O)_n$, A, etc.

In the present invention, compound (1) being a single compound means the same compound group except that it has a distribution in the number of n. In a case where $(C_mF_{2m}O)_n$ is $\{(CF_2O)_{n1}(CF_2CF_2O)_{n2}\}$, it means the same compound group except that it has a distribution in n1 and n2, and in a case where $(C_mF_{2m}O)_n$ is represented by $\{(CF_2O)_{n1/n}(CF_2CF_2O)_{n2/n}\}_n$, it means the same compound group except that it has a distribution in the number of n. Commercially available compound (10) is usually a compound which may be deemed to be a single compound in the above meaning, and therefore, its derivative having no change observed in its $\{(CF_2O)_{n1}(CF_2CF_2O)_{n2}\}$ portion may be deemed to be a single compound so long as other portions ($D^1$, $R^{f1}$, A, etc.) are the same.

The number average molecular weight of compound (1) is preferably from 2,000 to 10,000. When the number average molecular weight is within such a range, compound (1) is excellent in abrasion resistance. The number average molecular weight of compound (1) is more preferably from 2,100 to 9,000, particularly preferably from 2,400 to 8,000.

Usually, with a fluorinated ether compound, the chemical bond to a substrate is considered to become strong as the number average molecular weight becomes small. The reason is considered to be such that the number of hydrolysable silyl groups present per unit molecular weight becomes large. However, the present inventors have confirmed that if the number average molecular weight is less than the lower limit value within the above range, the abrasion resistance is likely to decrease. Further, if the number average molecular weight exceeds the upper limit value within the above range, the abrasion resistance decreases. The reason is considered to be such that the influence by the decrease in the number of hydrolysable silyl groups present per unit molecular weight becomes large.

[Fluorinated Ether Composition]

The fluorinated ether composition of the present invention (hereinafter referred to as the present composition) is a composition comprising compound (1) and a fluorinated ether compound other than compound (1). A fluorinated ether compound other than compound (1) (hereinafter referred to as another fluorinated ether compound) may, for example, be a fluorinated ether compound formed as a byproduct during the production of compound (1), or a known (particularly commercially available) fluorinated ether compound to be used for the same use as compound (1). Such another fluorinated ether compound is preferably a compound which is less likely to impair the properties of compound (1), and its relative content to compound (1) in the composition is preferably in such a small amount that is less likely to impair the properties of compound (1).

In a case where another fluorinated ether compound is a fluorinated ether compound formed as a byproduct during the production of compound (1), purification of compound (1) in the production of compound (1) becomes easy, and the purification step may be simplified. In a case where another fluorinated ether compound is a known fluorinated ether compound to be used for the same use as compound (1), a new advantageous effect such as to supplement the properties of compound (1) may sometimes be obtainable.

As another fluorinated ether compound, the following compound (2) or compound (6) is preferred, since it is less likely to impair the properties of compound (1).

(Compound (2))

Compound (2) is a fluorinated ether compound represented by the following formula (2).

$$D^2\text{-}R^{f2}\text{—}O\text{—}CH_2\text{—}(C_pF_{2p}O)_q\text{—}C_dF_{2d}\text{—}CH_2\text{—}O\text{—}$$
$$R^{f3}\text{-}D^3 \qquad (2)$$

wherein each of $D^2$ and $D^3$ which are independent of each other, is $CF_3$— or $CF_3$—O—; each of $R^{f2}$ and $R^{f3}$ which are independent of each other, is a $C_{1\text{-}20}$ fluoroalkylene group, or a $C_{2\text{-}20}$ fluoroalkylene group having an etheric oxygen atom between carbon-carbon atoms; d is an integer of from 1 to 5; p is an integer of from 1 to 6; q is an integer of from 1 to 200, provided that when q is 2 or more, $(C_pF_{2p}O)_q$ may be made of two or more types of $C_pF_{2p}O$ different in p.

$((C_pF_{2p}O)_q)$ p is preferably the same as m in the formula (1), since a compound formed as a byproduct during the production of compound (1) can be effectively utilized.

When p is 2 or more, $C_pF_{2p}$ may be linear or branched, but is preferably linear with a view to sufficiently imparting fingerprint stain removability and lubricity to the surface layer.

q is preferably the same as n in the formula (1), since a compound formed as a byproduct during the production of compound (1) can be effectively utilized.

When q is 2 or more, $(C_pF_{2p}O)_q$ may be made of two or more types of $C_pF_{2p}O$ different in p.

In a case where two or more types of $C_pF_{2p}O$ different in p are present in $(C_pF_{2p}O)_q$, the bond order of the respective $C_pF_{2p}O$ is not limited.

$(C_pF_{2p}O)_q$ is preferably the same as $(C_mF_{2m}O)_n$ in the formula (1), since a compound formed as a byproduct during the production of compound (1) can be effectively utilized. For example, in a case where the compound (1) is a compound having $\{(CF_2O)_{n1}(CF_2CF_2O)_{n2}\}$, it is particularly preferred that compound (2) is also a compound having $\{(CF_2O)_{n1}(CF_2CF_2O)_{n2}\}$.

In a case where compound (2) is a compound having $\{(CF_2O)_{n1}(CF_2CF_2O)_{n2}\}$, compound (2) is preferably a derivative of the above-mentioned compound (10), from the viewpoint of the production efficiency of compound (2) and from such a viewpoint that a compound formed as a byproduct during the production of compound (1) can effectively be utilized. In a case where compound (2) is a derivative of compound (10), —CH$_2$—$(C_pF_{2p}O)_q$— is —CH$_2$CF$_2$—O{(CF$_2$O)$_{n1}$(CF$_2$CF$_2$O)$_{n2}$}—, and —C$_d$F$_{2d}$— is —CF$_2$—.
(Group $R^{f2}$ and $R^{f3}$)

Examples and preferred examples of $R^{f2}$ and $R^{f3}$ are the same as of the above-mentioned $R^{f1}$.

Each of $R^{f2}$ and $R^{f3}$ is preferably a group represented by the above-mentioned formula (3-1), a group represented by the formula (3-2), or a group represented by the formula (3-3), from such a viewpoint that a compound formed as a byproduct during the production of compound (1) can effectively be utilized. Here, in $R^{f2}$, $R^F$ is a group bonded to $D^2$, and in $R^{f3}$, $R^F$ is a group bonded to $D^3$.
(Preferred Embodiments of Compound (2))

Compound (2) is preferably compound (21), compound (22) or compound (23), from such a viewpoint that a compound formed as a byproduct during the production in a preferred embodiment of compound (1) can effectively be utilized. Here, types of the two $R^F$ groups in each formula may be the same or different.

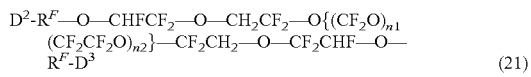

(21)

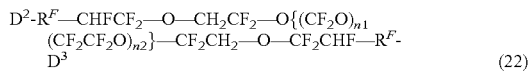

(22)

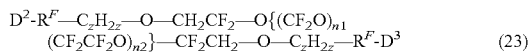

(23)

(Compound (6))

Compound (6) is a fluorinated ether compound represented by the following formula (6):

(6)

wherein each of $R^{F1}$ and $R^{F2}$ which are independent of each other, is a $C_{1-6}$ perfluoroalkyl group; s is an integer of from 1 to 6; and t is an integer of from 1 to 200, provided that when t is 2 or more, $(C_sF_{2s}O)_t$ may be made of two or more types of $C_sF_{2s}O$ different in s.

Compound (6) is obtainable by fluorinating compound (2) with fluorine gas. Otherwise, a commercially available product may be employed. Commercial products may, for example, be FOMBLIN M, FOMBLIN Y and FOMBLIN Z (manufactured by Solvay Solexis), Krytox (manufactured by DuPont), Demnum (manufactured by Daikin Kogyo K.K.), etc. FOMBLIN M and FOMBLIN Z wherein $(C_sF_{2s}O)_t$ contains $(CF_2O)$ and $(CF_2CF_2O)$, are preferred, since they are excellent in lubricity.

The fluorinated ether composition of the present invention may contain impurities in addition to compound (1) and another fluorinated ether compound. Impurities in addition to compound (1) and another fluorinated ether compound, are meant for compounds inevitably included during the production of compound (1) and another fluorinated ether compound, and they are compounds which do not contain a fluorinated ether chain such as $(C_mF_{2m}O)_n$. Specifically, they are byproducts formed during the process for producing compound (1) and another fluorinated ether compound, and components included during the process for producing compound (1) and another fluorinated ether compound.

The content of compound (1) in the present composition is preferably at least 70 mass %, particularly preferably at least 80 mass %. Here, the content of compound (1) in the present composition is meant for the content of compound (1) to the total amount of compound (1), another fluorinated ether compound and impurities such as the above mentioned byproducts in the present composition.

That is, the total content of another fluorinated ether compound and the impurities, to the total amount of compound (1), another fluorinated ether compound and the impurities in the present composition, is preferably at most 30 mass %, particularly preferably at most 20 mass %. When the content of compound (1) is within the above range, the surface layer will be excellent in initial water/oil repellency, abrasion resistance, fingerprint stain removability, lubricity and uniformity.

However, in a case where another fluorinated ether compound is compound (2) and/or compound (6), since they are compounds which are less likely to impair the properties of compound (1) as mentioned above, the preferred content of compound (1) in the present composition may be lower than the lower limit of the above content.

In a case where the present composition contains at least one of compound (2) and compound (6), the total content of compound (1), compound (2) and compound (6) in the present composition is preferably at least 80 mass %, particularly preferably at least 85 mass %. Here, the total content of compound (1), compound (2) and compound (6) in the present composition is meant for the total content of compound (1), compound (2) and compound (6) to the total amount of compound (1), another fluorinated ether compound and impurities such as the above-mentioned byproducts in the present composition.

That is, the total content of the impurities and another fluorinated ether compound other than compound (2) and compound (6), is preferably at most 20 mass %, particularly preferably at most 15 mass %. When the total content of compound (1), compound (2) and compound (6) is within the above range, the surface layer will be excellent in initial water/oil repellency, abrasion resistance, fingerprint stain removability, lubricity and uniformity.

In a case where the present composition contains compound (2), the mass ratio of compound (1) to compound (2) in the present composition (compound (1)/compound (2)) is preferably at least 40/60 and less than 100/0, particularly preferably at least 50/50 and less than 100/0. When compound (1)/compound (2) is within the above range, the surface layer will be excellent in initial water/oil repellency, abrasion resistance, fingerprint stain removability, lubricity and uniformity.

In a case where the present composition contains compound (6), the mass ratio of compound (1) to compound (6)

in the present composition (compound (1)/compound (6)) is preferably at least 40/60 and less than 100/0, particularly preferably at least 50/50 and less than 100/0. When compound (1)/compound (6) is within the above range, the surface layer will be excellent in initial water/oil repellency, abrasion resistance, fingerprint stain removability, lubricity and uniformity.

In a case where the present composition contains compound (2) and compound (6), the mass ratio of compound (1) to the total amount of compound (2) and compound (6) in the present composition (compound (1)/[compound (2)+compound (6)]) is preferably at least 40/60 and less than 100/0, particularly preferably at least 50/50 and less than 100/0. When compound (1)/[compound (2)+compound (6)] is within the above range, the surface layer will be excellent in initial water/oil repellency, abrasion resistance, fingerprint stain removability, lubricity and uniformity.

[Coating Liquid]

The coating liquid of the present invention (hereinafter referred to as the present coating liquid) comprises compound (1) or the present composition, and a medium. The medium is preferably liquid. The present coating liquid may be a solution or a dispersion so long as it is liquid. Hereinafter, the present compound (1) and the present composition may generally be referred to as compound (1), etc.

So long as it contains compound (1), etc., the present coating liquid may contain impurities such as byproducts formed in a process for producing compound (1).

The concentration of compound (1), etc. is preferably from 0.001 to 10 mass %, particularly preferably from 0.1 to 1 mass %, in the present coating liquid.

(Medium)

The medium is preferably an organic solvent. The organic solvent may be a fluorinated organic solvent or a non-fluorinated organic solvent, or it may contain both solvents.

The fluorinated organic solvent may, for example, be a fluorinated alkane, a fluorinated aromatic compound, a fluoroalkyl ether, a fluorinated alkylamine or a fluoroalcohol.

The fluorinated alkane is preferably a $C_{4-8}$ compound. Commercial products may, for example, be $C_6F_{13}H$ (trade name: AC-2000, manufactured by Asahi Glass Co., Ltd.), $C_6F_{13}C_2H_5$ (trade name: AC-6000, manufactured by Asahi Glass Co., Ltd.), $C_2F_5CHFCHFCF_3$ (trade name: Vertrel, manufactured by DuPont), etc.

The fluorinated aromatic compound may, for example, be hexafluorobenzene, trifluoromethylbenzene, perfluorotoluene, bis(trifluoromethyl)benzene, etc.

The fluoroalkyl ether is preferably a $C_{4-12}$ compound. Commercial products may, for example, be $CF_3CH_2OCF_2CF_2H$ (trade name: AE-3000, manufactured by Asahi Glass Co., Ltd.), $C_4F_9OCH_3$ (trade name: Novec-7100, manufactured by 3M), $C_4F_9OC_2H_5$ (trade name: Novec-7200, manufactured by 3M), $C_6F_{13}OCH_3$ (trade name: Novec-7300, manufactured by 3M), etc.

The fluorinated alkylamine may, for example, be perfluorotripropylamine, perfluorotributylamine, etc.

The fluoroalcohol may, for example, be 2,2,3,3-tetrafluoropropanol, 2,2,2-trifluoroethanol, hexafluoroisopropanol, etc.

From the viewpoint of the solubility of compound (1), the fluorinated organic solvent is preferably a fluorinated alkane, a fluorinated aromatic compound or a fluoroalkyl ether, particularly preferably a fluoroalkyl ether.

The non-fluorinated organic solvent is preferably a compound composed solely of hydrogen atoms and carbon atoms, or a compound composed solely of hydrogen atoms, carbon atoms and oxygen atoms, and a hydrocarbon type organic solvent, an alcohol type organic solvent, a ketone type organic solvent, an ether type organic solvent, or an ester type organic solvent, may be mentioned.

The hydrocarbon type organic solvent is preferably hexane, heptane, cyclohexane, etc.

The alcohol type organic solvent is preferably methanol, ethanol, 1-propanol, 2-propanol, etc.

The ketone type organic solvent is preferably acetone, methyl ethyl ketone, methyl isobutyl ketone, etc.

The ether type organic solvent is preferably diethyl ether, tetrahydrofuran, tetraethylene glycol dimethyl ether, etc.

The ester type organic solvent is preferably ethyl acetate, butyl acetate, etc.

From the viewpoint of the solubility of compound (1), the non-fluorinated organic solvent is particularly preferably a ketone type organic solvent.

The medium is preferably at least one organic solvent selected from the group consisting of a fluorinated alkane, a fluorinated aromatic compound, a fluoroalkyl ether, a compound composed solely of hydrogen atoms and carbon atoms, and a compound composed solely of hydrogen atoms, carbon atoms and oxygen atoms. Particularly preferred is a fluorinated organic solvent selected from a fluorinated alkane, a fluorinated aromatic compound and a fluoroalkyl ether.

With a view to increasing the solubility of compound (1), the medium preferably contains at least one organic solvent selected from the group consisting of a fluorinated alkane, a fluorinated aromatic compound and a fluoroalkyl ether, as fluorinated organic solvents, and a compound composed solely of hydrogen atoms, carbon atoms and oxygen atoms, as a non-fluorinated organic solvent, in an amount, in total, of at least 90 mass % of the entire medium.

The present coating liquid contains the medium in an amount of preferably from 90 to 99.999 mass %, particularly preferably from 99 to 99.9 mass %.

The present coating liquid may contain other components in addition to compound (1), etc. and the medium, within a range not to impair the effects of the present invention.

Other components may, for example, be known additives such as an acid catalyst or basic catalyst to accelerate the hydrolysis and condensation reaction of hydrolysable silyl groups.

The acid catalyst may, for example, be hydrochloric acid, nitric acid, acetic acid, sulfuric acid, phosphoric acid, sulfonic acid, methane sulfonic acid, p-toluene sulfonic acid, etc.

The basic catalyst may, for example, be sodium hydroxide, potassium hydroxide, ammonia, etc.

In the present coating liquid, the content of such other components is preferably at most 10 mass %, particularly preferably at most 1 mass %.

The solid content concentration in the present coating liquid is preferably from 0.001 to 10 mass %, particularly preferably from 0.01 to 1 mass %. The solid content concentration in the present coating liquid is a value calculated from the mass of the coating liquid before heating and the mass after heating for 4 hours in a convection dryer at 120° C. Further, the concentration of the present composition can be calculated from the solid content concentration and the charged amounts of the present composition, the solvent, etc.

[Substrate Having Surface Layer]

The substrate having a surface layer of the present invention, has a surface layer formed from compound (1), etc.

(Surface Layer)

In compound (1), etc., a hydrolysable silyl group ($-SiL_cR_{3-c}$) in compound (1) undergoes a hydrolytic reaction to form a silanol group (Si—OH), and such silanol groups undergo an intermolecular dehydration condensation reaction to form a Si—O—Si bond, or such a silanol group undergoes a dehydration condensation reaction with a hydroxy group on the surface of a substrate (substrate-OH) to form a chemical bond (substrate-O—Si). That is, the surface layer in the present invention contains compound (1) in such a state that some or all of hydrolysable silyl groups in compound (1) have become silanol groups or have further undergone a dehydration condensation reaction.

(Substrate)

The substrate in the present invention is not particularly limited so long as it is a substrate, for which it is required to impart water/oil repellency. The material for the substrate may, for example, be a metal, a resin, glass, ceramics, a stone, or a composite material thereof.

(Touch Panel)

As the surface layer is formed from compound (1), etc., excellent initial water/oil repellency is imparted, and at the same time, it is possible to obtain excellent abrasion resistance whereby the water/oil repellency scarcely decreases even if the surface is repeatedly rubbed, a performance (fingerprint stain removability) whereby fingerprint stains on the surface can easily be removed, smoothness (lubricity) when the surface is touched by a finger, and uniformity (transparency, planarity, little irregularities) of the surface layer. Accordingly, the substrate having such a surface layer thus obtainable, is useful as a member constituting a touch panel, since the surface layer has excellent initial water/oil repellency, and at the same time, has excellent abrasion resistance, fingerprint stain removability, lubricity and uniformity. The touch panel is meant for an input device in an input/display device (touch panel device) having a display device combined with a device to input a contact position information by touching with e.g. a finger. The touch panel is constituted by a substrate and, depending upon the input detecting system, a transparent conductive film, electrodes, wiring, IC, etc. By using the side having the surface layer of the substrate as the input surface of a touch panel, it is possible to obtain a touch panel wherein the surface layer has excellent abrasion resistance, fingerprint stain removability, lubricity and uniformity.

The material for the touch panel has translucency. Here, "has translucency" means that the normal incidence visible light transmittance in accordance with JIS R3106 is at least 25%.

The material for the touch panel substrate is preferably glass or a transparent resin. The glass is preferably soda lime glass, alkali aluminosilicate glass, borosilicate glass, alkali-free glass, crystal glass or quartz glass, and chemically tempered soda lime glass, chemically tempered alkali aluminosilicate glass and chemically tempered borosilicate glass are particularly preferred. The transparent resin is preferably an acrylic resin or a polycarbonate resin.

Further, the substrate in the present invention is suitable also as a display substrate constituting the outermost surface of various displays such as liquid crystal display, CRT display, projection display, plasma display, EL display, etc. By forming a surface layer by surface treatment using compound (1), etc. or the present coating liquid, it is possible to obtain a display wherein the surface layer has excellent abrasion resistance, fingerprint stain removability, lubricity and uniformity.

[Method for Producing Substrate Having Surface Layer]

(Dry Coating Method)

Compound (1), etc. can be used as they are, in a method for producing a substrate having a surface layer by treating the surface of the substrate by a dry coating method. Compound (1), etc. are suitable for forming a surface layer excellent in adhesion, by a dry coating method. The dry coating method may, for example, be a technique such as vacuum vapor deposition, CVD or sputtering. With a view to preventing decomposition of compound (1) and from the viewpoint of simplicity of the apparatus, a vacuum vapor deposition method may suitably be employed. The vacuum vapor deposition method may further be divided into a resistance heating method, an electron beam heating method, a high frequency induction heating method, a reactive vapor deposition method, a molecular beam epitaxy method, a hot wall vapor deposition method, an ion plating method, a cluster ion beam method, etc., and any one of them may be used. With a view to preventing decomposition of compound (1) and from the viewpoint of simplicity of the apparatus, a resistance heating method may suitably be employed. The vacuum vapor deposition method is not particularly limited, and a conventional apparatus may be employed.

In the case of using a vacuum vapor deposition method, film-deposition conditions may vary depending upon the type of the vacuum vapor deposition method to be employed, but in the case of a resistance heating method, the degree of vacuum before vapor deposition is preferably at most $1\times10^{-2}$ Pa, particularly preferably at most $1\times10^{-3}$ Pa. The heating temperature for the vapor deposition source is not particularly limited so long as it is a temperature at which the vapor deposition source such as compound (1), etc. has a sufficient vapor pressure. Specifically, it is preferably from 30 to 400° C., particularly preferably from 50 to 300° C. When the heating temperature is at least the lower limit value in the above range, the film-deposition rate will be good. When it is at most the upper limit value in the above range, it is possible to impart initial water/oil repellency, abrasion resistance and fingerprint stain removability to the surface of the substrate without decomposition of compound (1). At the time of vacuum vapor deposition, the substrate temperature is preferably within a range of from room temperature (20 to 25° C.) to 200° C. When the substrate temperature is at most 200° C., the film-deposition rate will be good. The upper limit value of the substrate temperature is more preferably at most 150° C., particularly preferably at most 100° C.

In the case of treating the surface of a substrate by a dry coating method using compound (1), etc., the surface layer to be formed on the surface of the substrate by such treatment preferably has a film thickness of from 1 to 100 nm, particularly preferably from 1 to 50 nm. When the film thickness of the surface layer is at least the lower limit value in the above range, the effects by the surface treatment tend to be sufficiently obtainable, and when it is at most the upper limit value in the above range, the utilization efficiency will be high. Here, the film thickness can be calculated, for example, from the oscillation period of an interference pattern of reflected X-rays obtained by an X-ray reflectance method by means of an X-ray diffractometer ATX-G (manufactured by RIGAKU CORPORATION) for thin film analysis.

Particularly in the vacuum vapor deposition method, the content of compound (1) in the present composition is large, and the content of impurities is small, whereby the effects for improving initial water/oil repellency, abrasion resistance and fingerprint stain removability will be large. This is considered to be such that byproducts having small molecular weights as impurities tend to vapor-deposit on the surface of a substrate prior to vapor deposition of compound (1), and as a result, chemical bonding between compound (1) and the substrate surface, which plays a role of developing the performance, will not be thereby inhibited.

(Wet Coating Method)

It is possible to produce a substrate having a surface layer by applying the present coating liquid on the surface of a substrate, followed by drying.

As the method for applying the coating liquid, a known technique may suitably be employed.

The coating method is preferably a spin coating method, a wipe coating method, a spray coating method, a squeegee coating method, a dip coating method, a die coating method, an ink jet method, a flow coating method, a roll coating method, a casting method, a Langmuir-Blodgett technique or a gravure coating method.

The method for drying may be any method so long as it is capable of drying and removing the medium, and a known method may suitably be employed. The drying temperature is preferably from 10 to 300° C., particularly preferably from 20 to 200° C.

The surface layer formed on the surface of the substrate after drying and removing the medium preferably has a film thickness of from 1 to 100 nm, particularly preferably from 1 to 50 nm. When the film thickness of the surface layer is at least the lower limit value in the above range, the effects by the surface treatment tend to be sufficiently obtainable, and when it is at most the upper limit value in the above range, the utilization efficiency will be high. Here, the film thickness can be measured in the same manner as in the method for measuring the film thickness of the surface layer formed by the dry coating method.

(Post Treatment)

After forming a surface layer on a substrate surface by the above dry coating method or wet coating method, an operation to accelerate a reaction between compound (1) and the substrate may be conducted, as the case requires, in order to improve the durability of the surface layer against abrasion. As such an operation, heating, humidification, light irradiation, etc. may be mentioned. For example, by heating the substrate having the surface layer formed, in the atmospheric air with a moisture, it is possible to accelerate a reaction such as a hydrolytic reaction of hydrolysable silyl groups to silanol groups, a reaction of silanol groups with hydroxy groups, etc. on the substrate surface, or formation of siloxane bonds by a condensation reaction of silanol groups.

After the surface treatment, compounds in the surface layer, which are not chemically bonded to other compounds or the substrate, may be removed as the case requires. A specific method may, for example, be a method of washing the surface layer with a solvent, or a method of wiping with a cloth impregnated with a solvent.

EXAMPLES

Now, the present invention will be described in further detail with reference to Examples, but it should be understood that the present invention is by no means limited to such Examples.

Hereinafter, "%" means "mass %" unless otherwise specified. Further, a mixture composed of two or more types of compound (1) will be referred to as a "compound", and a mixture composed of compound (1) and another fluorinated ether compound will be referred to as a "composition".

Ex. 1 to 2, 5 to 6, 11 to 12, 15 to 16, and 21 to 24 are Examples of the present invention, and Ex. 3 to 4, 7, 13 to 14, and 17 are Comparative Examples.

[Ex. 1: Production of Compound (A)]

(Ex. 1-1)

Into a 300 mL three-necked flask, 2.9 g of a 20% KOH aqueous solution, 33 g of tert-butyl alcohol, 110 g of 1,3-bis(trifluoromethyl)benzene, and 220 g of compound (10) (trade name: FLUOROLINK D4000, manufactured by Solvay Solexis) were put, and 14.6 g of $CF_3CF_2CF_2$—O—CF=$CF_2$ was added. In a nitrogen atmosphere, the mixture was stirred at 40° C. for 20 hours. After washing once with a dilute hydrochloric acid aqueous solution, an organic phase was recovered and concentrated by an evaporator to obtain 233 g of crude product (a). Crude product (a) was diluted with 115 g of $C_6F_3H$ (trade name: AC-2000, manufactured by Asahi Glass Co., Ltd.) and then developed and fractionated by silica gel column chromatography. As developing solvents, AC-2000, AC-2000/$CF_3CH_2OCF_2CF_2H$ (trade name: AE-3000, manufactured by Asahi Glass Co., Ltd.) (mass ratio: 1/2), and AE-3000/acetone (mass ratio: 2/1) were sequentially used. With respect to each fraction, the structure of terminal groups, and the average value of the number of constituting units (n1-1, n2) were obtained from the integrated value of $^1$H-NMR and $^{19}$F-NMR. It was thereby found that in crude product (a), compound (11-1), compound (21-1) and compound (10) were contained in amounts of 50 mol %, 25 mol % and 25 mol %, respectively. Further, 105.1 g (yield: 44.8%) of compound (11-1) and 55.4 g (yield: 23.6%) of compound (21-1) were obtained.

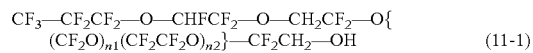

(11-1)

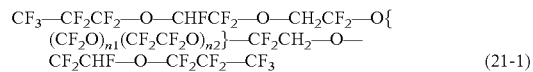

(21-1)

(10)

NMR Spectra of Compound (11-1):
$^1$H-NMR (300.4 MHz, solvent: $CDCl_3$, standard: TMS) δ (ppm): 3.9 (2H), 4.2 (2H), 5.8 to 6.0 (1H).
$^{19}$F-NMR (282.7 MHz, solvent: $CDCl_3$, standard: $CFCl_3$) δ (ppm): −52.4 to −55.8 (42F), −78.8 (1F), −80.8 (1F), −81.4 (1F), −82.2 (3F), −83.5 (1F), −85.3 to −88.2 (2F), −89.4 to −91.1 (82F), −130.5 (2F), −145.1 (1F).
Average value of the number of units n1: 21
Average value of the number of units n2: 20
Number average molecular weight: 4,200

NMR Spectra of Compound (21-1):
$^1$H-NMR (300.4 MHz, solvent: $CDCl_3$, standard: TMS) δ (ppm): 4.2 (4H), 5.8 to 6.0 (2H).
$^{19}$F-NMR (282.7 MHz, solvent: $CDCl_3$, standard: $CFCl_3$) δ (ppm): −52.4 to −55.8 (42F), −78.8 (2F), −80.7 (2F), −82.2 (6F), −85.3 to −88.2 (4F), −89.4 to −91.1 (84F), −130.5 (4F), −145.1 (2F).
Average value of the number of units n1: 21
Average value of the number of units n2: 20
Number average molecular weight: 4,400

(Ex. 1-2)

Into a 100 mL two-necked eggplant flask, 52.0 g of compound (11-1) obtained in Ex. 1-1, 0.52 g of tetrabutylammonium hydrogen sulfate, 4.4 g of allyl bromide, and 6.5 g of a 30% sodium hydroxide aqueous solution were added and stirred at 60° C. for 8 hours. After completion of the reaction, 50 g of AC-2000 was added, followed by washing once with a dilute hydrochloric acid aqueous solution, and an organic phase was recovered. The recovered organic phase was passed through silica gel column, and the recovered solution was concentrated by an evaporator to obtain 52.4 g (yield: 99.9%) of compound (12-1).

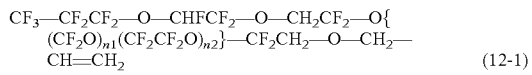

NMR Spectra of Compound (12-1):

$^1$H-NMR (300.4 MHz, solvent: CDCl$_3$, standard: TMS) δ (ppm): 3.7 (2H), 4.1 (2H), 4.2 (2H), 5.2 to 5.3 (2H), 5.8 to 6.0 (2H).

$^{19}$F-NMR (282.7 MHz, solvent: CDCl$_3$, standard: CFCl$_3$) δ (ppm): −52.3 to −55.7 (42F), −78.1 (1F), −78.7 (1F), −80.2 (1F), −80.7 (1F), −82.2 (3F), −85.4 to −88.2 (2F), −89.4 to −91.1 (82F), −130.5 (2F), −145.1 (1F).

Average value of the number of units n1: 21
Average value of the number of units n2: 20
Number average molecular weight: 4,200

(Ex. 1-3)

Into a 50 mL closed pressure resistant container made of polytetrafluoroethylene, 5.0 g of compound (12-1) obtained in Ex. 1-2, 0.034 g of di-tert-butyl peroxide, 1.26 g of trichlorosilane and 2.5 g of AC-2000 were put and stirred at 120° C. for 8 hours. After removing unreacted substances, solvent, etc. by concentration under reduced pressure, the reaction solution was put into a flask equipped with a dropping funnel, and 1.0 g of a mixed solution of trimethyl orthoformate and methanol (molar ratio of trimethyl orthoformate/methanol=25/1) was dropwise added and reacted at 60° C. for 3 hours. After completion of the reaction, the solvent, etc. were distilled off under reduced pressure, and to the residue, 0.05 g of activated carbon was added, followed by stirring for one hour, whereupon filtration was conducted by a membrane filter with a pore size of 0.5 μm, to obtain 5.0 g (yield: 97.2%) of compound (A) being a mixture of compound (111a-1) and compound (111b-1). The molar ratio of compound (111a-1) to compound (111b-1) was 92:8 from NMR.

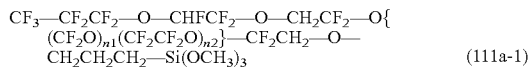

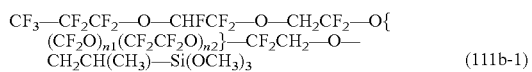

NMR Spectra of Compound (111a-1):

$^1$H-NMR (300.4 MHz, solvent: CDCl$_3$, standard: TMS) δ (ppm): 0.7 (2H), 1.7 (2H), 3.6 (11H), 3.8 (2H), 4.2 (2H), 5.8 to 6.0 (1H).

$^{19}$F-NMR (282.7 MHz, solvent: CDCl$_3$, standard: CFCl$_3$) δ (ppm): −52.3 to −55.7 (42F), −78.2 (1F), −78.7 (1F), −80.3 (1F), −80.7 (1F), −82.2 (3F), −85.4 to −88.2 (2F), −89.4 to −91.1 (82F), −130.5 (2F), −145.1 (1F).

Average value of the number of units n1: 21
Average value of the number of units n2: 20
Number average molecular weight: 4,300

NMR Spectra of Compound (111b-1):

$^1$H-NMR (300.4 MHz, solvent: CDCl$_3$, standard: TMS) δ (ppm): 1.1 (3H), 1.8 (1H), 3.6 (11H), 3.8 (2H), 4.2 (2H), 5.8 to 6.0 (1H).

$^{19}$F-NMR (282.7 MHz, solvent: CDCl$_3$, standard: CFCl$_3$) δ (ppm): −52.3 to −55.7 (42F), −78.1 (1F), −78.7 (1F), −80.2 (1F), −80.7 (1F), −82.2 (3F), −85.4 to −88.2 (2F), −89.4 to −91.1 (82F), −130.5 (2F), −145.1 (1F).

Average value of the number of units n1: 21
Average value of the number of units n2: 20
Number average molecular weight: 4,300

[Ex. 2: Production of Composition (B)]

(Ex. 2-1)

Into a 100 mL eggplant flask made of a tetrafluoroethylene/perfluoro(alkoxy vinyl ether) copolymer (PFA), 25.0 g of compound (12-1) obtained in Ex. 1-2, 0.16 g of a xylene solution of a platinum/1,3-divinyl-1,1,3,3-tetramethyldisiloxane complex (platinum content: 2%), 2.84 g of trimethoxysilane, and 12.5 g of AC-2000, were put and stirred at 70° C. for 10 hours. After completion of the reaction, the solvent, etc. were distilled off under reduced pressure, and to the residue, 0.2 g of activated carbon was added, followed by stirring for one hour, whereupon filtration was conducted by a membrane filter with a pore size of 0.5 μm, to obtain 24.5 g (yield: 95.3%) of composition (B) comprising compound (111a-1) and compound (30). The molar ratio of compound (111a-1) to compound (30) was 83:17 from NMR.

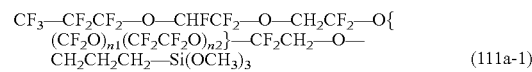

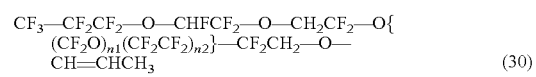

NMR Spectra of Compound (111a-1):

$^1$H-NMR (300.4 MHz, solvent: CDCl$_3$, standard: TMS) δ (ppm): 0.7 (2H), 1.7 (2H), 3.6 (11H), 3.8 (2H), 4.2 (2H), 5.8 to 6.0 (1H).

$^{19}$F-NMR (282.7 MHz, solvent: CDCl$_3$, standard: CFCl$_3$) δ (ppm): −52.3 to −55.7 (42F), −78.2 (1F), −78.7 (1F), −80.3 (1F), −80.7 (1F), −82.2 (3F), −85.4 to −88.2 (2F), −89.4 to −91.1 (82F), −130.5 (2F), −145.1 (1F).

Average value of the number of units n1: 21
Average value of the number of units n2: 20
Number average molecular weight: 4,300

NMR Spectra of Compound (30):

$^1$H-NMR (300.4 MHz, solvent: CDCl$_3$, standard: TMS) δ (ppm): 1.6 (3H), 4.0 (2H), 4.2 (2H), 4.5 to 5.0 (1H), 5.8 to 6.2 (2H).

$^{19}$F-NMR (282.7 MHz, solvent: CDCl$_3$, standard: CFCl$_3$) δ (ppm): −52.3 to −55.7 (42F), −78.1 (1F), −78.7 (1F), −80.2 (1F), −80.7 (1F), −82.2 (3F), −85.4 to −88.2 (2F), −89.4 to −91.1 (82F), −130.5 (2F), −145.1 (1F).

Average value of the number of units n1: 21
Average value of the number of units n2: 20
Number average molecular weight: 4,200

[Ex. 3: Production of Composition (C)]

(Ex. 3-1)

Into a 100 mL two-necked eggplant flask, 30.0 g of compound (10), 0.64 g of tetrabutylammonium hydrogen sulfate, 4.5 g of allyl bromide, and 6.0 g of a 30% sodium hydroxide aqueous solution were added and stirred at 60° C. for 8 hours. After completion of the reaction, 30 g of AC-2000 was added, followed by washing once with a dilute hydrochloric acid aqueous solution, and an organic phase was recovered. The recovered organic phase was passed through silica gel column, and the recovered solution was concentrated by an evaporator to obtain 29.7 g (yield: 97.1%) of compound (31).

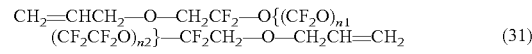

NMR Spectra of Compound (31):

$^1$H-NMR (300.4 MHz, solvent: CDCl$_3$, standard: TMS) δ (ppm): 3.7 (4H), 4.1 (4H), 5.2 to 5.3 (4H), 5.9 (2H).

$^{19}$F-NMR (282.7 MHz, solvent: CDCl$_3$, standard: CFCl$_3$) δ (ppm): −52.3 to −55.7 (42F), −78.1 (2F), −80.2 (2F), −89.4 to −91.1 (80F).

Average value of the number of units n1: 21
Average value of the number of units n2: 20
Number average molecular weight: 4,000

(Ex. 3-2)

Into a 100 mL eggplant flask made of PFA, 29.6 g of compound (31) obtained in Ex. 3-1, 0.42 g of a xylene solution of a platinum/1,3-divinyl-1,1,3,3-tetramethyldisiloxane complex (platinum content: 2%), 5.34 g of trimethoxysilane, and 15 g of AC-2000, were put and stirred at 70° C. for 10 hours. After completion of the reaction, the solvent, etc. were distilled off under reduced pressure, and to the residue, 0.1 g of activated carbon was added, followed by stirring for one hour, whereupon filtration was conducted by a membrane filter with a pore size of 0.5 μm, to obtain 29.1 g (yield: 92.1%) of composition (C). The structure of terminal groups in composition (C) was obtained from the integrated values of $^1$H-NMR and $^{19}$F-NMR, and found to contain —OCH$_2$CH$_2$CH$_2$Si(OCH$_3$)$_3$ and —OCH═CHCH$_3$ in amounts of 84 mol % and 16 mol %, respectively. That is, composition (C) is considered to contain 71 mol % of compound (32), 26 mol % of compound (33) and 3 mol % of compound (34).

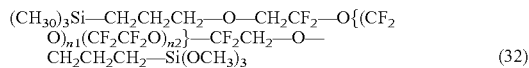

(32)

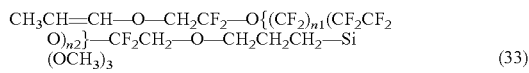

(33)

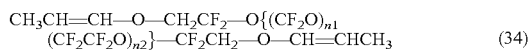

(34)

NMR Spectra of Composition (C):

$^1$H-NMR (300.4 MHz, solvent: CDCl$_3$, standard: TMS) δ (ppm): 0.7 (3.36H), 1.6 (0.96H), 1.7 (3.36H), 3.6 (18.5H), 3.8 (3.36H), 4.0 (0.64H), 4.5 to 5.0 (0.32H), 5.8 to 6.2 (0.32H).

$^{19}$F-NMR (282.7 MHz, solvent: CDCl$_3$, standard: CFCl$_3$) δ (ppm): −52.3 to −55.7 (42F), −78.2 (2F), −80.3 (2F), −89.1 to −91.0 (80F).

Average value of the number of units n1: 21
Average value of the number of units n2: 20
Number average molecular weight: 4,200

[Ex. 4: Production of Composition (D)]

(Ex. 4-1)

Into a 100 mL eggplant flask, 30.0 g of compound (11-1) obtained in Ex. 1-1, 0.9 g of sodium fluoride powder, and 30 g of dichloropentafluoropropane (trade name: AK-225, manufactured by Asahi Glass Co., Ltd.) were put, and 3.5 g of CF$_3$CF$_2$CF$_2$OCF(CF$_3$)COF was added. In a nitrogen atmosphere, the mixture was stirred at 50° C. for 24 hours. After removing the sodium fluoride powder by a pressure filtration apparatus, excess CF$_3$CF$_2$CF$_2$OCF(CF$_3$)COF and AK-225 were distilled off under reduced pressure. The obtained crude product was diluted with AC-2000 and passed through a silica gel column, and the recovered solution was concentrated by an evaporator to obtain 31.8 g (yield: 98.8%) of compound (35).

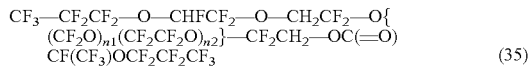

(35)

NMR Spectra of Compound (35):

$^1$H-NMR (300.4 MHz, solvent: CDCl$_3$, standard: TMS) δ (ppm): 4.2 (2H), 4.7 (2H), 5.8 to 6.0 (1H).

$^{19}$F-NMR (282.7 MHz, solvent: CDCl$_3$, standard: CFCl$_3$) δ (ppm): −52.4 to −55.8 (42F), −78.8 to −88.2 (17F), −89.4 to −91.1 (82F), −130.3 (2F), −130.5 (2F), −132.5 (1F), −145.1 (1F).

Average value of the number of units n1: 21
Average value of the number of units n2: 20
Number average molecular weight: 4,500

(Ex. 4-2)

An autoclave (made of nickel, internal capacity: 1 L) was prepared, and at a discharge outlet of the autoclave, a condenser maintained at 20° C., a NaF pellet-packed layer and a condenser maintained at 0° C., were set in series. Further, a liquid-returning line to return a condensed liquid from the condenser maintained at 0° C. to the autoclave was set.

Into the autoclave, 750 g of ClCF$_2$CFClCF$_2$OCF$_2$CF$_2$Cl (hereinafter referred to as CFE-419) was put and stirred while maintaining the temperature at 25° C. After blowing nitrogen gas into the autoclave at 25° C. for one hour, 20% fluorine gas was blown into it at 25° C. at a flow rate of 2.0 L/hr for one hour. Then, while blowing 20% fluorine gas at the same flow rate, a solution having 31.0 g of compound (35) obtained in Ex. 4-1 dissolved in 124 g of CFE-419, was injected into the autoclave over a period of 4.3 hours.

Then, while blowing 20% fluorine gas at the same flow rate, the internal pressure of the autoclave was raised to 0.15 MPa (gauge pressure). Into the autoclave, 4 mL of a benzene solution containing 0.05 g/mL of benzene in CFE-419 was injected while heating from 25° C. to 40° C., whereupon the benzene solution-injection inlet of the autoclave was closed. After stirring for 15 minutes, 4 mL of the benzene solution was injected again while maintaining the temperature at 40° C., whereupon the injection inlet was closed. The same operation was further repeated three times. The total amount of benzene injected was 0.17 g.

Further, while blowing 20% fluorine gas at the same flow rate, stirring was continued for one hour. Then, the pressure of the autoclave was returned to the atmospheric pressure, and nitrogen gas was blown into the autoclave for one hour. The content of the autoclave was concentrated by an evaporator to obtain 31.1 g (yield: 98.5%) of compound (36).

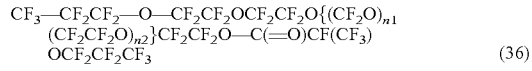

(36)

NMR Spectra of Compound (36):

$^{19}$F-NMR (282.7 MHz, solvent: CDCl$_3$, standard: CFCl$_3$) δ (ppm): −52.4 to −55.7 (42F), −78.8 to −88.1 (11F), −89.4 to −91.1 (92F), −91.5 (2F), −130.3 (2F), −130.5 (2F), −132.5 (1F).

Average value of the number of units n1: 21
Average value of the number of units n2: 20
Number average molecular weight: 4,600

(Ex. 4-3)

Into a round-bottomed flask made of PFE, 30.0 g of compound (36) obtained in Ex. 4-2 and 60 g of AK-225 were put. While cooling in an ice bath, the mixture was stirred, and in a nitrogen atmosphere, 2.0 g of methanol was slowly dropwise added from a dropping funnel. While bubbling with nitrogen, stirring was continued for 12 hours.

The reaction mixture was concentrated by an evaporator to obtain 27.6 g (yield: 98.8%) of compound (37).

(37)

NMR Spectra of Compound (37):

$^1$H-NMR (300.4 MHz, solvent: CDCl$_3$, standard: TMS) δ (ppm): 3.9 (3H).

$^{19}$F-NMR (282.7 MHz, solvent: CDCl$_3$, standard: CFCl$_3$) δ (ppm): −52.4 to −55.8 (42F), −82.2 (3F), −89.4 to −91.1 (92F), −130.5 (2F).

Average value of the number of units n1: 21
Average value of the number of units n2: 20
Number average molecular weight: 4,200

(Ex. 4-4)

In 100 mL three-necked eggplant flask, 0.18 g of lithium chloride was dissolved in 18.3 g of ethanol. 25.0 g of compound (37) obtained in Ex. 4-3 was added thereto, and while cooling in an ice bath, a solution having 0.75 g of sodium borohydride dissolved in 22.5 g of ethanol, was slowly dropwise added. Thereafter, the ice bath was removed, and stirring was continued while slowly raising the temperature to room temperature. After stirring at room temperature for 12 hours, an aqueous hydrochloric acid solution was dropwise added until the liquid became acidic. 20 mL of AC-2000 was added, followed by washing once with water and once with a saturated sodium chloride aqueous solution, whereupon the organic phase was recovered. The recovered organic phase was concentrated by an evaporator to obtain 24.6 g (yield: 99.0%) of compound (38).

NMR Spectra of Compound (38):
$^1$H-NMR (300.4 MHz, solvent: CDCl$_3$, standard: TMS) δ (ppm): 3.9 (2H).
$^{19}$F-NMR (282.7 MHz, solvent: CDCl$_3$, standard: CFCl$_3$) δ (ppm): −52.4 to −55.7 (42F), −81.4 (1F), −82.2 (3F), −83.4 (1F), −89.4 to −91.1 (90F), −130.5 (2F).
Average value of the number of units n1: 21
Average value of the number of units n2: 20 Number average molecular weight: 4,200
(Ex. 4-5)
Into a 100 mL two-necked eggplant flask, 20.0 g of compound (38) obtained in Ex. 4-4, 0.21 g of tetrabutylammonium hydrogen sulfate, 1.76 g of allyl bromide, and 2.6 g of a 30% sodium hydroxide aqueous solution were added and stirred at 60° C. for 8 hours. After completion of the reaction, 20 g of AC-2000 was added, followed by washing once with a dilute hydrochloric acid aqueous solution, and an organic phase was recovered. The recovered organic phase was passed through silica gel column, and the recovered solution was concentrated by an evaporator to obtain 19.8 g (yield: 98.2%) of compound (39).

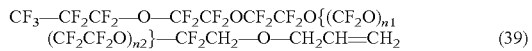

NMR Spectra of Compound (39):
$^1$H-NMR (300.4 MHz, solvent: CDCl$_3$, standard: TMS) δ (ppm): 3.7 (2H), 4.1 (2H), 5.2 to 5.3 (2H), 5.9 (1H).
$^{19}$F-NMR (282.7 MHz, solvent: CDCl$_3$, standard: CFCl$_3$) δ (ppm): −52.3 to −55.7 (42F), −78.1 (1F), −80.1 (1F), −82.1 (3F), −89.4 to −91.1 (90F), −130.5 (2F).
Average value of the number of units n1: 21
Average value of the number of units n2: 20
Number average molecular weight: 4,300
(Ex. 4-6)
Into a 100 mL eggplant flask made of PFA, 10.0 g of compound (39) obtained in Ex. 4-5, 0.09 g of a xylene solution of a platinum/1,3-divinyl-1,1,3,3-tetramethyldisiloxane complex (platinum content: 2%), 1.48 g of trimethoxysilane, and 5.0 g of AC-2000, were put and stirred at 70° C. for 10 hours. After completion of the reaction, the solvent, etc. were distilled off under reduced pressure, and to the residue, 0.1 g of activated carbon was added, followed by stirring for one hour, whereupon filtration was conducted by a membrane filter with a pore size of 0.5 μm, to obtain 9.9 g (yield: 96.4%) of composition (D) comprising compound (40) and compound (41). The molar ratio of compound (40) to compound (41) was 82:18 from NMR.

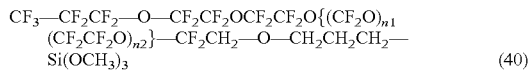

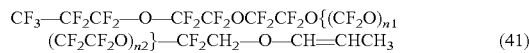

NMR Spectra of Compound (40):
$^1$H-NMR (300.4 MHz, solvent: CDCl$_3$, standard: TMS) δ (ppm): 0.7 (2H), 1.7 (2H), 3.6 (11H), 3.8 (2H).
$^{19}$F-NMR (282.7 MHz, solvent: CDCl$_3$, standard: CFCl$_3$) δ (ppm): −52.4 to −55.8 (42F), −78.2 (1F), −80.2 (1F), −82.2 (3F), −89.4 to −91.1 (90F), −130.5 (2F).
Average value of the number of units n1: 21
Average value of the number of units n2: 20
Number average molecular weight: 4,400
NMR Spectra of Compound (41):
$^1$H-NMR (300.4 MHz, solvent: CDCl$_3$, standard: TMS) δ (ppm): 1.6 (3H), 4.0 (2H), 4.5 to 5.0 (1H), 5.9 to 6.2 (1H).
$^{19}$F-NMR (282.7 MHz, solvent: CDCl$_3$, standard: CFCl$_3$) δ (ppm): −52.4 to −55.8 (42F), −78.2 (1F), −80.2 (1F), −82.2 (3F), −89.4 to −91.1 (90F), −130.5 (2F).
Average value of the number of units n1: 21
Average value of the number of units n2: 20
Number average molecular weight: 4,300
[Ex. 5: Production of Composition (E)]
(Ex. 5-1)
Into a 200 mL three-necked flask, 1.5 g of a 20% KOH aqueous solution, 15 g of tert-butyl alcohol, 50 g of 1,3-bis (trifluoromethyl)benzene, and 100 g of compound (10) were put, and 11.6 g of CF$_3$CF$_2$CF$_2$—O—CF(CF$_3$)CF$_2$—O—CF=CF$_2$ was added. In a nitrogen atmosphere, the mixture was stirred at 40° C. for 20 hours. After washing once with a dilute hydrochloric acid aqueous solution, an organic phase was recovered and concentrated by an evaporator to obtain 109 g of crude product (b). Crude product (b) was diluted with 55 g of AC-2000 and then developed and fractionated by silica gel column chromatography. As developing solvents, AC-2000, AC-2000/AE-3000, (mass ratio: 1/2), and AE-3000/acetone (mass ratio: 2/1) were sequentially used. With respect to each fraction, the structure of terminal groups, and the average value of the number of constituting units (n1-1, n2) were obtained from the integrated value of $^1$H-NMR and $^{19}$F-NMR. It was thereby found that in crude product (b), compound (11-2), compound (21-2) and compound (10) were contained in amounts of 50 mol %, 25 mol % and 25 mol %, respectively. Further, 43.6 g (yield: 39.1%) of compound (11-2) and 27.0 g (yield: 24.2%) of compound (21-2) were obtained.

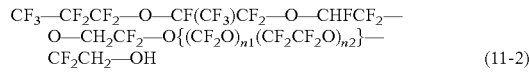

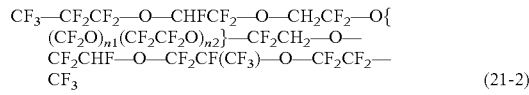

NMR Spectra of Compound (11-2):
$^1$H-NMR (300.4 MHz, solvent: CDCl$_3$, standard: TMS) δ (ppm): 3.9 (2H), 4.2 (2H), 5.8 to 6.0 (1H).
$^{19}$F-NMR (282.7 MHz, solvent: CDCl$_3$, standard: CFCl$_3$) δ (ppm): −52.4 to −55.8 (42F), −78.9 (1F), −80.9 (4F), −81.4 (1F), −82.2 (5F), −83.5 (1F), −84.4 to −87.2 (2F), −89.1 to −90.7 (86F), −130.2 (2F), −145.5 (2F).
Average value of the number of units n1: 21
Average value of the number of units n2: 21
Number average molecular weight: 4,400

NMR Spectra of Compound (21-2):
$^1$H-NMR (300.4 MHz, solvent: CDCl$_3$, standard: TMS) δ (ppm): 4.2 (4H), 5.8 to 6.0 (2H).
$^{19}$F-NMR (282.7 MHz, solvent: CDCl$_3$, standard: CFCl$_3$) δ (ppm): −52.4 to −55.8 (42F), −78.9 (2F), −80.9 (8F), −82.2 (10F), −84.3 to −87.2 (4F), −89.1 to −90.8 (88F), −130.2 (4F), −145.5 (4F).
Average value of the number of units n1: 21
Average value of the number of units n2: 21
Number average molecular weight: 4,600

(Ex. 5-2)

Into a 100 mL three-necked eggplant flask, 30.0 g of compound (11-2) obtained in Ex. 5-1, 0.30 g of tetrabutylammonium hydrogen sulfate, 4.1 g of allyl bromide, and 3.6 g of a 30% sodium hydroxide aqueous solution were added and stirred at 60° C. for 8 hours. After completion of the reaction, 50 g of AC-2000 was added, followed by washing once with a dilute hydrochloric acid aqueous solution, and an organic phase was recovered. The recovered organic phase was passed through silica gel column, and the recovered solution was concentrated by an evaporator to obtain 28.6 g (yield: 94.5%) of compound (12-2).

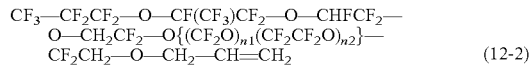
(12-2)

NMR Spectra of Compound (12-2):
$^1$H-NMR (300.4 MHz, solvent: CDCl$_3$, standard: TMS) δ (ppm): 3.7 (2H), 4.1 (2H), 4.2 (2H), 5.2 to 5.3 (2H), 5.8 to 6.0 (2H).
$^{19}$F-NMR (282.7 MHz, solvent: CDCl$_3$, standard: CFCl$_3$) δ (ppm): −52.3 to −55.7 (42F), −78.1 (1F), −78.7 (1F), −80.2 (1F), −80.7 (4F), −82.2 (5F), −84.4 to −87.2 (2F), −89.1 to −91.0 (86F), −130.2 (2F), −145.51 (2F).
Average value of the number of units n1: 21
Average value of the number of units n2: 21
Number average molecular weight: 4,500

(Ex. 5-3)

10.0 g of compound (12-2) obtained in Ex. 5-2, 0.19 g of a xylene solution of a platinum/1,3-divinyl-1,1,3,3-tetramethyldisiloxane complex (platinum content: 2%), 1.37 g of trimethoxysilane, and 5.0 g of AC-2000, were put and stirred at 70° C. for 10 hours. After completion of the reaction, the solvent, etc. were distilled off under reduced pressure, and to the residue, 0.2 g of activated carbon was added, followed by stirring for one hour, whereupon filtration was conducted by a membrane filter with a pore size of 0.5 µm, to obtain 10.1 g (yield: 98.3%) of composition (E) comprising compound (111a-2) and compound (30-2). The molar ratio of compound (111a-2) to compound (30-2) was 81:19 from NMR.

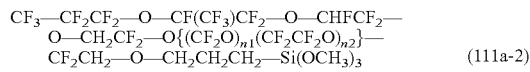
(111a-2)

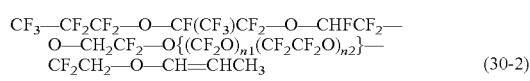
(30-2)

NMR Spectra of Compound (111a-2):
$^1$H-NMR (300.4 MHz, solvent: CDCl$_3$, standard: TMS) δ (ppm): 0.7 (2H), 1.7 (2H), 3.6 (11H), 3.8 (2H), 4.2 (2H), 5.8 to 6.0 (1H).
$^{19}$F-NMR (282.7 MHz, solvent: CDCl$_3$, standard: CFCl$_3$) δ (ppm): −52.0 to −55.8 (42F), −78.2 (1F), −78.8 (1F), −80.4 (1F), −80.9 (4F), −82.2 (5F), −84.4 to −87.1 (2F), −89.1 to −91.7 (86F), −130.2 (2F), −145.5 (2F).
Average value of the number of units n1: 21
Average value of the number of units n2: 21
Number average molecular weight: 4,600

NMR Spectra of Compound (30-2):
$^1$H-NMR (300.4 MHz, solvent: CDCl$_3$, standard: TMS) δ (ppm): 1.6 (3H), 4.0 (2H), 4.2 (2H), 4.5 to 5.0 (1H), 5.8 to 6.2 (2H).
$^{19}$F-NMR (282.7 MHz, solvent: CDCl$_3$, standard: CFCl$_3$) δ (ppm): −52.0 to −55.8 (42F), −78.2 (1F), −78.8 (1F), −80.4 (1F), −80.9 (4F), −82.2 (5F), −84.4 to −87.1 (2F), −89.1 to −91.7 (86F), −130.2 (2F), −145.5 (2F).
Average value of the number of units n1: 21
Average value of the number of units n2: 21
Number average molecular weight: 4,500

[Ex. 6: Production of Composition (F)]

(Ex. 6-1)

The following compound (10-3) was obtained by the method disclosed in Ex. 1 to 4 in WO2004/035656.

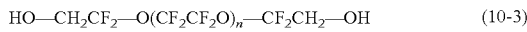
(10-3)

NMR Spectra of Compound (10-3):
$^1$H-NMR (300.4 MHz, solvent: CDCl$_3$, standard: TMS) δ (ppm): 3.9 (4H).
$^{19}$F-NMR (282.7 MHz, solvent: CDCl$_3$, standard: CFCl$_3$) δ (ppm): −81.4 (4F), −89.5 (80F).
Average value of the number of units n: 20
Number average molecular weight: 2,500

(Ex. 6-2)

Into a 100 mL three-necked flask, 0.72 g of a 20% KOH aqueous solution, 7.5 g of tert-butyl alcohol, 25 g of 1,3-bis(trifluoromethyl)benzene, and 50.0 g of compound (10-3) obtained in Ex. 6-1 were put, and 5.40 g of CF$_3$CF$_2$CF$_2$—O—CF=CF$_2$ was added. In a nitrogen atmosphere, the mixture was stirred at 40° C. for 20 hours. After washing once with a dilute hydrochloric acid aqueous solution, an organic phase was recovered and concentrated by an evaporator to obtain 53.8 g of crude product (c). Crude product (c) was diluted with 115 g of AC-2000 and then developed and fractionated by silica gel column chromatography. As developing solvents, AC-2000, AC-2000/AE-3000 (mass ratio: 1/4), and AE-3000/acetone (mass ratio: 2/1) were sequentially used. With respect to each fraction, the structure of terminal groups, and the average value of the number of constituting units (n2) were obtained from the integrated value of $^1$H-NMR and $^{19}$F-NMR. It was thereby found that in crude product (c), compound (11-3), compound (21-3) and compound (10-3) were contained in amounts of 52 mol %, 24 mol % and 24 mol %, respectively. Further, 24.0 g (yield: 44.0%) of compound (11-3) and 13.1 g (yield: 24.0%) of compound (21-3) were obtained.

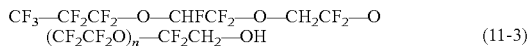
(11-3)

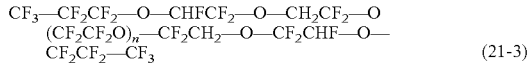
(21-3)

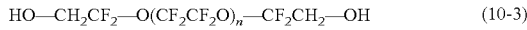
(10-3)

NMR Spectra of Compound (11-3):
$^1$H-NMR (300.4 MHz, solvent: CDCl$_3$, standard: TMS) δ (ppm): 3.9 (2H), 4.2 (2H), 5.8 to 6.0 (1H).
$^{19}$F-NMR (282.7 MHz, solvent: CDCl$_3$, standard: CFCl$_3$) δ (ppm): −78.8 (2F), −81.4 (2F), −82.2 (3F), −85.3 to −88.2 (2F), −89.5 (80F), −90.0 to −91.5 (2F), −130.5 (2F), −145.1 (1F).
Average value of the number of units n: 20
Number average molecular weight: 2,800

NMR Spectra of Compound (21-3):
$^1$H-NMR (300.4 MHz, solvent: CDCl$_3$, standard: TMS) δ (ppm): 4.2 (4H), 5.8 to 6.0 (2H).
$^{19}$F-NMR (282.7 MHz, solvent: CDCl$_3$, standard: CFCl$_3$) δ (ppm): −78.8 (4F), −82.2 (6F), −85.3 to −88.2 (4F), −89.5 (80F), −90.0 to −91.5 (4F), −130.5 (4F), −145.1 (2F).

Average value of the number of units n: 20
Number average molecular weight: 3,000

(Ex. 6-3)

Into a 100 mL two-necked eggplant flask, 20.0 g of compound (11-3) obtained in Ex. 6-2, 0.31 g of tetrabutylammonium hydrogen sulfate, 4.4 g of allyl bromide, and 3.2 g of a 30% sodium hydroxide aqueous solution were added and stirred at 60° C. for 8 hours. After completion of the reaction, 20 g of AC-2000 was added, followed by washing once with a dilute hydrochloric acid aqueous solution, and an organic phase was recovered. The recovered organic phase was passed through silica gel column, and the recovered solution was concentrated by an evaporator to obtain 20.0 g (yield: 98.6%) of compound (12-3).

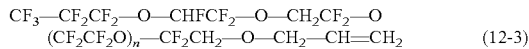

$CF_3-CF_2CF_2-O-CHFCF_2-O-CH_2CF_2-O$
$(CF_2CF_2O)_n-CF_2CH_2-O-CH_2-CH=CH_2$  (12-3)

NMR Spectra of Compound (12-3):
$^1$H-NMR (300.4 MHz, solvent: CDCl$_3$, standard: TMS) δ (ppm): 3.7 (2H), 4.1 (2H), 4.2 (2H), 5.2 to 5.3 (2H), 5.8 to 6.0 (2H).
$^{19}$F-NMR (282.7 MHz, solvent: CDCl$_3$, standard: CFCl$_3$) δ (ppm): −78.1 (2F), −78.7 (2F), −82.2 (3F), −85.4 to −88.2 (2F), −89.5 (80F), −90.0 to −91.5 (2F), −130.5 (2F), −145.1 (1F).
Average value of the number of units n: 20
Number average molecular weight: 2,800

(Ex. 6-4)

Into a 100 mL eggplant flask made of PFA, 18.0 g of compound (12-3) obtained in Ex. 6-3, 0.13 g of a xylene solution of a platinum/1,3-divinyl-1,1,3,3-tetramethyldisiloxane complex (platinum content: 2%), 2.27 g of trimethoxysilane, and 10.0 g of AC-2000, were put and stirred at 70° C. for 10 hours. After completion of the reaction, the solvent, etc. were distilled off under reduced pressure, and to the residue, 0.1 g of activated carbon was added, followed by stirring for one hour, whereupon filtration was conducted by a membrane filter with a pore size of 0.5 μm, to obtain 18.2 g (yield: 96.9%) of composition (F) comprising compound (111a-3) and compound (30-3). The molar ratio of compound (111a-3) to compound (30-3) was 80:20 from NMR.

$CF_3-CF_2CF_2-O-CHFCF_2-O-CH_2CF_2-O$
$(CF_2CF_2O)_n-CF_2CH_2-O-CH_2CH_2CH_2-Si$
$(OCH_3)_3$  (111a-3)

$CF_3-CF_2CF_2-O-CHFCF_2-O-CH_2CF_2-O$
$(CF_2CF_2O)_n-CF_2CH_2-O-CH=CHCH_3$  (30-3)

NMR Spectra of Compound (111a-3):
$^1$H-NMR (300.4 MHz, solvent: CDCl$_3$, standard: TMS) δ (ppm): 0.7 (2H), 1.7 (2H), 3.6 (11H), 3.8 (2H), 4.2 (2H), 5.8 to 6.0 (1H).
$^{19}$F-NMR (282.7 MHz, solvent: CDCl$_3$, standard: CFCl$_3$) δ (ppm): −78.1 (2F), −78.7 (2F), −82.2 (3F), −85.4 to −88.2 (2F), −89.5 (80F), −90.0 to −91.5 (2F), −130.5 (2F), −145.1 (1F).
Average value of the number of units n: 20
Number average molecular weight: 2,900

NMR Spectra of Compound (30-3):
$^1$H-NMR (300.4 MHz, solvent: CDCl$_3$, standard: TMS) δ (ppm): 1.6 (3H), 4.0 (2H), 4.2 (2H), 4.5 to 5.0 (1H), 5.8 to 6.2 (2H).
$^{19}$F-NMR (282.7 MHz, solvent: CDCl$_3$, standard: CFCl$_3$) δ (ppm): −78.1 (2F), −78.7 (2F), −82.2 (3F), −85.4 to −88.2 (2F), −89.5 (80F), −90.0 to −91.5 (2F), −130.5 (2F), −145.1 (1F).
Average value of the number of units n: 20
Number average molecular weight: 2,800

[Ex. 7: Production of Composition (G)]

(Ex. 7-1)

Using the following compound (42) (trade name: Uniox M-1000, manufactured by NOF Corporation, average value of n2: 21), the following compound (43) was obtained in the same manner as in the method disclosed in Ex. 1 in WO2004/008380.

$CH_3O(CH_2CH_2O)_n-CH_2CH_2-OH$  (42)

$CF_3O(CF_2CF_2O)_n-CF_2CH_2-OH$  (43)

NMR Spectra of Compound (43):
$^1$H-NMR (300.4 MHz, solvent: CDCl$_3$, standard: TMS) δ (ppm): 3.9 (2H).
$^{19}$F-NMR (282.7 MHz, solvent: CDCl$_3$, standard: CFCl$_3$) δ (ppm): −56.2 (3F), −81.4 (2F), −89.5 (82F), −91.4 (2F).
Average value of the number of units n: 21
Number average molecular weight: 2,600

(Ex. 7-2)

Into a 100 mL two-necked eggplant flask, 25.0 g of compound (43) obtained in Ex. 7-1, 0.40 g of tetrabutylammonium hydrogen sulfate, 5.8 g of allyl bromide, and 4.0 g of a 30% sodium hydroxide aqueous solution were added and stirred at 60° C. for 8 hours. After completion of the reaction, 20 g of AC-2000 was added, followed by washing once with a dilute hydrochloric acid aqueous solution, and an organic phase was recovered. The recovered organic phase was passed through silica gel column, and the recovered solution was concentrated by an evaporator to obtain 24.5 g (yield: 96.4%) of compound (44).

$CF_3O(CF_2CF_2O)_n-CF_2CH_2-O-CH_2-CH=CH_2$  (44)

NMR Spectra of Compound (44):
$^1$H-NMR (300.4 MHz, solvent: CDCl$_3$, standard: TMS) δ (ppm): 3.8 (2H), 4.1 (2H), 5.2 to 5.3 (2H), 5.9 (1H).
$^{19}$F-NMR (282.7 MHz, solvent: CDCl$_3$, standard: CFCl$_3$) δ (ppm): −56.3 (3F), −78.3 (2F), −89.5 (82F), −91.5 (2F).
Average value of the number of units n: 21
Number average molecular weight: 2,600

(Ex. 7-3)

Into a 100 mL eggplant flask made of PFA, 20.0 g of compound (44) obtained in Ex. 7-2, 0.14 g of a xylene solution of a platinum/1,3-divinyl-1,1,3,3-tetramethyldisiloxane complex (platinum content: 2%), 2.50 g of trimethoxysilane, and 10.0 g of AC-2000, were put and stirred at 70° C. for 10 hours. After completion of the reaction, the solvent, etc. were distilled off under reduced pressure, and to the residue, 0.1 g of activated carbon was added, followed by stirring for one hour, whereupon filtration was conducted by a membrane filter with a pore size of 0.5 μm, to obtain 20.0 g (yield: 95.6%) of composition (G) comprising compound (45) and compound (46). The molar ratio of compound (45) to compound (46) was 83:17 from NMR.

$CF_3O(CF_2CF_2O)_n-CF_2CH_2-O-CH_2CH_2CH_2-Si$
$(OCH_3)_3$  (45)

$CF_3O(CF_2CF_2O)_n-CF_2CH_2-O-CH=CHCH_3$  (46)

NMR Spectra of Compound (45):
$^1$H-NMR (300.4 MHz, solvent: CDCl$_3$, standard: TMS) δ (ppm): 0.7 (2H), 1.7 (2H), 3.6 (11H), 3.8 (2H).
$^{19}$F-NMR (282.7 MHz, solvent: CDCl$_3$, standard: CFCl$_3$) δ (ppm): −56.3 (3F), −78.3 (2F), −89.5 (82F), −91.5 (2F).
Average value of the number of units n: 21
Number average molecular weight: 2,800

NMR Spectra of Compound (46):
$^1$H-NMR (300.4 MHz, solvent: CDCl$_3$, standard: TMS) δ (ppm): 1.6 (3H), 4.0 (2H), 4.5 to 5.0 (1H), 5.8 to 6.2 (1H).
$^{19}$F-NMR (282.7 MHz, solvent: CDCl$_3$, standard: CFCl$_3$) δ (ppm): −56.3 (3F), −78.3 (2F), −89.5 (82F), −91.5 (2F).

Average value of the number of units n: 21
Number average molecular weight: 2,600

[Ex. 11 to 17: Production and Evaluation of Substrate Having Surface Layer]

Surface treatment of a substrate was conducted by using each of compounds and compositions obtained in Ex. 1 to 7, and designated as Ex. 11 to 17. In each Ex., a substrate having a surface layer was prepared by using each of the following dry coating method, wet coating method, spin coating method and spray coating method. As the substrate, chemically tempered glass was used. With respect to the substrate having a surface layer thus obtained, evaluations were conducted by the following methods. The results are shown in Table 1.

(Dry Coating Method)

Dry coating was conducted by means of a vacuum vapor deposition apparatus (VTR-350M, manufactured by ULVAC, Inc.) (vacuum vapor deposition method). 0.5 g of the compound or composition obtained in Ex. 1 to 7 was filled in a boat made of molybdenum in the vacuum vapor deposition apparatus, and inside of the vacuum vapor deposition apparatus was evacuated to $1 \times 10^{-3}$ Pa or less. The boat having the compound or composition placed therein was heated at a temperature-raising rate of at most 10° C./min, and at the time when the vapor deposition rate by a crystal oscillation film-thickness meter exceeded 1 nm/sec., a shutter was opened to initiate film deposition onto the surface of the substrate. At the time when the film thickness became about 50 nm, the shutter was closed to terminate film deposition onto the surface of the substrate. The substrate having the compound or composition deposited thereon was heat-treated at 200° C. for 30 minutes and then cleaned with AK-225 to obtain a substrate having a surface layer.

(Wet Coating Method)

The compound or composition obtained in Ex. 1 to 7 and $C_4F_9OC_2H_5$ (trade name: Novec-7200, manufactured by 3M) as a medium, were mixed to prepare a coating liquid having a solid content concentration of 0.05%. A substrate was dipped in the coating liquid (dip coating method), and after being left for 30 minutes, the substrate was withdrawn. The substrate was dried at 200° C. for 30 minutes and then cleaned with AK-225 to obtain a substrate having a surface layer.

(Evaluation Methods in Dry Coating Method and Wet Coating Method)

<Method for Measuring Water Contact Angle and n-Hexadecane Contact Angle>

The contact angle of about 2 μL of distilled water or n-hexadecane placed on the surface of the surface layer, was measured by means of a contact angle-measuring apparatus DM-500 (manufactured of Kyowa Interface Science Co., Ltd.). Measurements were carried out at 5 different locations on the surface of the surface layer, and the average value thereof was calculated. For the calculation of the contact angle, a 2θ method was employed.

<Initial Water and n-Hexadecane Contact Angles>

With respect to a substrate having a surface layer, the initial water contact angle and the initial n-hexadecane contact angle were measured by the above-measuring method.

<Abrasion Resistance>

With respect to a substrate having a surface layer, using a reciprocal traverse tester (manufactured by KNT) in accordance with JIS L0849, a cellulose non-woven fabric (BEMCOT M-3, manufactured by Asahi Kasei Corporation) was reciprocated 100,000 times under a load of 1 kg, whereupon the water contact angle and the n-hexadecane contact angle were measured.

The smaller the decrease in the water repellency (water contact angle) and oil repellency (n-hexadecane contact angle) as the number of abrasion times is increased, the smaller the decrease in the performance by the abrasion, and the better the abrasion resistance.

<Fingerprint Stain Removability>

An artificial fingerprint liquid (liquid composed of oleic acid and squalene) was deposited on a flat surface of a silicon rubber stopper, and then, excess oil was wiped off by a non-woven fabric (BEMCOT M-3, manufactured by Asahi Kasei Corporation) to prepare a fingerprint stamp. The fingerprint stamp was placed on a substrate having a surface layer and pressed for 10 seconds under a load of 1 kg. At that time, the haze at the portion where the fingerprint was deposited, was measured by a haze meter (manufactured by Toyo Seiki Co., Ltd.). The value at that time was taken as the initial value. Then, with respect to the portion where the fingerprint was deposited, using a reciprocal traverse tester (manufactured by KNT) having tissue paper attached, wiping was carried out under a load of 500 g. The haze value was measured after every one reciprocation for wiping, and if it reached a numerical value where the haze was no longer visually observed, before the end of 10 reciprocations for wiping, such a case was regarded as "pass".

<Dynamic Friction Coefficient>

The dynamic friction coefficient of a substrate having a surface layer, against an artificial skin (PBZ13001, manufactured by Idemitsu Technofine Co., Ltd.) was measured under conditions of a contact area of 3 cm×3 cm and a load of 100 g, by means of a load-variable friction/abrasion test system HHS2000 (manufactured by Shinto Scientific Co., Ltd.).

The smaller the dynamic friction coefficient, the better the lubricity.

(Spin Coating Method)

The compound or composition obtained in Ex. 1 to 7 and $C_4F_9OC_2H_5$ (trade name: Novec-7200, manufactured by 3M) as a medium, were mixed to prepare a coating liquid having a solid content concentration of 0.05%. The coating liquid was applied to the substrate by a spin coating method for 30 seconds under a condition of 1,500 rpm. The substrate was dried at 120° C. for 30 minutes and then cleaned with AK-225 to obtain a substrate having a surface layer.

(Spray Coating Method)

The compound or composition obtained in Ex. 1 to 7 and Novec-7200 as a medium, were mixed to prepare a coating liquid having a solid content concentration of 0.1%. The coating liquid was applied to the substrate by spray coating by means of a spray coating system (manufactured by Nordson). The substrate was dried at 120° C. for 30 minutes and then cleaned with AK-225 to obtain a substrate having a surface layer.

(Evaluation Methods in Spin Coating Method and Spray Coating Method)

<Method for Measuring Haze>

The haze of a substrate having a surface layer was measured by a haze meter (manufactured by Toyo Seiki Co., Ltd.). The smaller the haze, the better the uniformity of the surface layer.

<Method for Measuring Surface Roughness>

The surface roughness (Ra) of a substrate having a surface layer was measured by a scanning probe microscope SPM400 (manufactured by SII NanoTechnology Inc.)

The smaller the surface roughness (Ra), the better the uniformity of the surface layer.

<Method for Measuring Water Contact Angle>

The contact angle of about 2 μL of distilled water placed on the surface of the surface layer, was measured by means of a contact angle-measuring apparatus DM-500 (manufactured of Kyowa Interface Science Co., Ltd.). Measurements were carried out at 10 different locations on the surface of the surface layer of the substrate, and the average value thereof and the standard deviation were calculated.

The smaller the standard deviation, the smaller the difference in the contact angle among the respective measurement locations, and the better the uniformity of the surface layer.

sable silyl groups at both terminals (Ex. 3), the surface layer is poor in abrasion resistance and lubricity.

In Ex. 14 and 17 wherein compositions (D) and (G) containing a fluorinated ether compound of the formula (1) wherein $R^{f1}$ had no hydrogen atom, were used, the surface layer has a large surface roughness (Ra) and a large standard deviation of the water contact angle and thus is poor in uniformity, and also the haze is high.

[Ex. 21 to 24: Production and Evaluation of Substrate Having Surface Layer]

Surface treatment of a substrate was conducted by using a composition obtained by mixing composition (B) obtained

TABLE 1

| | | | Ex. | | | | | | |
|---|---|---|---|---|---|---|---|---|---|
| | | | 11 | 12 | 13 | 14 | 15 | 16 | 17 |
| | Fluorinated ether compound or composition | | (A) | (B) | (C) | (D) | (E) | (F) | (G) |
| Dry coating method | Water contact angle (degrees) | Initial | 110.9 | 112.3 | 109.5 | 112.8 | 112.7 | 112.4 | 113.3 |
| | | After 100,000 times of abrasion | 110.3 | 111.6 | 102.9 | 108.6 | 112.0 | 111.8 | 110.1 |
| | n-Hexadecane contact angle (degrees) | Initial | 65.2 | 65.4 | 65.9 | 66.3 | 65.6 | 66.1 | 67.0 |
| | | After 100,000 times of abrasion | 64.8 | 65.0 | 63.3 | 67.2 | 65.6 | 65.0 | 66.7 |
| | Fingerprint stain removability | | Pass | Pass | Pass | Pass | Pass | Pass | Pass |
| | Dynamic friction coefficient | | 0.26 | 0.25 | 0.40 | 0.22 | 0.27 | 0.41 | 0.38 |
| Wet coating method | Water contact angle (degrees) | Initial | 110.1 | 112.7 | 109.4 | 113.4 | 112.2 | 112.3 | 113.2 |
| | | After 100,000 times of abrasion | 109.8 | 109.4 | 97.2 | 108.5 | 110.1 | 109.9 | 108.9 |
| | n-Hexadecane contact angle (degrees) | Initial | 65.4 | 65.3 | 65.7 | 66.5 | 65.9 | 66.5 | 67.0 |
| | | After 100,000 times of abrasion | 64.8 | 64.1 | 56.0 | 66.1 | 65.4 | 66.0 | 65.9 |
| | Fingerprint stain removability | | Pass | Pass | Pass | Pass | Pass | Pass | Pass |
| | Dynamic friction coefficient | | 0.32 | 0.31 | 0.53 | 0.29 | 0.32 | 0.42 | 0.43 |
| Spin coating method | Haze (%) | | 0.03 | 0.04 | 0.33 | 0.19 | 0.03 | 0.04 | 0.22 |
| | Surface roughness (Ra) (nm) | | 0.43 | 0.47 | 3.16 | 1.57 | 0.39 | 0.41 | 1.80 |
| | Water contact angle | Average value (degrees) | 112.29 | 111.49 | 109.82 | 112.90 | 112.47 | 112.33 | 113.11 |
| | | Standard deviation | 0.43 | 0.47 | 0.70 | 0.94 | 0.41 | 0.40 | 0.99 |
| Spray coating method | Haze (%) | | 0.04 | 0.04 | 0.48 | 0.24 | 0.04 | 0.03 | 0.21 |
| | Surface roughness (Ra) (nm) | | 0.79 | 0.58 | 7.01 | 2.02 | 0.70 | 0.66 | 1.81 |
| | Water contact angle | Average value (degrees) | 111.78 | 111.60 | 110.09 | 113.01 | 112.10 | 112.05 | 113.42 |
| | | Standard deviation | 0.43 | 0.36 | 0.64 | 0.92 | 0.40 | 0.33 | 0.88 |

In Ex. 11 wherein compound (A) was used as compound (1), and in Ex. 12 and 15 to 16 wherein compositions (B), (E) and (F) were used as the present composition, the surface layer has high initial water/oil repellency and is excellent in abrasion resistance, fingerprint stain removability and lubricity and excellent also in uniformity.

On the other hand, in Ex. 13 wherein composition (C) containing a fluorinated ether compound having hydrolyin Ex. 2, and compound (21-1) obtained in Ex. 1 or compound (6-1) (trade name: FOMBLIN M03, manufactured by Solvay Solexis) in a blend ratio shown in Table 2, and designated as Ex. 21 to 24. In each Ex., a substrate having a surface layer was prepared by using each of the dry coating method and the wet coating method in the same manner as in Ex. 11 to 14, and evaluated by the same method. The results are shown in Table 2.

TABLE 2

| | | | Ex. | | | | |
|---|---|---|---|---|---|---|---|
| | | | 12 | 21 | 22 | 23 | 24 |
| Blend ratio (mass ratio) Ex. 12, 21 to 23: composition (B)/compound (21-1) Ex. 24: composition (B)/compound (6-1) | | | 100/0 | 90/10 | 70/30 | 50/50 | 70/30 |
| Dry coating method | Water contact angle (degrees) | Initial | 112.3 | 108.6 | 106.1 | 111.7 | 112.4 |
| | | After 100,000 times of abrasion | 111.6 | 106.5 | 106.9 | 111.6 | 108.1 |
| | n-Hexadecane contact angle (degrees) | Initial | 65.4 | 63.7 | 63.2 | 64.4 | 66.0 |
| | | After 100,000 times of abrasion | 65.0 | 63.9 | 62.8 | 64.2 | 65.8 |
| | Fingerprint stain removability | | Pass | Pass | Pass | Pass | Pass |
| | Dynamic friction coefficient | | 0.25 | 0.22 | 0.24 | 0.25 | 0.22 |

TABLE 2-continued

| | | | Ex. | | | | |
|---|---|---|---|---|---|---|---|
| | | | 12 | 21 | 22 | 23 | 24 |
| Wet coating method | Water contact angle (degrees) | Initial | 112.7 | 111.5 | 111.5 | 109.4 | 113.1 |
| | | After 100,000 times of abrasion | 109.4 | 109.6 | 110.8 | 109.3 | 108.2 |
| | n-Hexadecane contact angle (degrees) | Initial | 65.3 | 66.3 | 66.2 | 65.0 | 66.3 |
| | | After 100,000 times of abrasion | 64.1 | 64.4 | 64.0 | 64.0 | 65.4 |
| | Fingerprint stain removability | | Pass | Pass | Pass | Pass | Pass |
| | Dynamic friction coefficient | | 0.31 | 0.35 | 0.31 | 0.33 | 0.29 |

In Ex. 21 to 24 wherein a composition having compound (21-1) or compound (6-1) added to composition (B) (Ex. 2) as the present composition, was used, the surface layer has high initial water/oil repellency and is excellent in abrasion resistance, fingerprint stain removability and lubricity, like in Ex. 12 wherein composition (B) (Ex. 2) as the present composition was used.

INDUSTRIAL APPLICABILITY

The fluorinated ether compound of the present invention is useful for surface treatment to impart water/oil repellency to a surface of a substrate, such as a member constituting a surface of a touch panel to be touched by a finger.

What is claimed is:

1. A fluorinated ether compound represented by the following formula (1):

$$D^1-R^{f1}-O-CH_2-(C_mF_{2m}O)_n-A \quad (1)$$

wherein $D^1$ is $CF_3-$ or $CF_3-O-$; $R^{f1}$ is a $C_{1-20}$ fluoroalkylene group containing at least one hydrogen atom, a $C_{2-20}$ fluoroalkylene group containing at least one hydrogen atom and having an etheric oxygen atom between carbon-carbon atoms, a $C_{1-20}$ alkylene group, or a $C_{2-20}$ alkylene group having an etheric oxygen atom between carbon-carbon atoms; A is a group represented by the following formula (4); m is an integer of from 1 to 6; and
n is an integer of from 1 to 200, provided that when n is 2 or more, $(C_mF_{2m}O)_n$ may be made of two or more types of $C_mF_{2m}O$ different in m;

$$-C_aF_{2a}-B-C_bH_{2b}-SiL_cR_{3-c} \quad (4)$$

wherein B is a single bond, or $-C_gH_{2g}O-$, $-C_hH_{2h}O-C(=O)NH-$ or $-C(=O)-NH-$; L is a hydrolysable group; R is a hydrogen atom or a monovalent hydrocarbon group; a is an integer of from 1 to 5; b is an integer of from 1 to 10; c is an integer of from 1 to 3; g is an integer of from 1 to 5; and h is an integer of from 1 to 5.

2. The fluorinated ether compound according to claim 1, wherein $-CH_2-(C_mF_{2m}O)_n$ is $-CH_2CF_2-O\{(CF_2O)_{n1}(CF_2CF_2O)_{n2}\}$ (wherein n1 is an integer of at least 1, n2 is an integer of at least 1, n1+n2 is an integer of from 2 to 200, and the bond order of n1 $CF_2O$ and n2 $CF_2CF_2O$ is not limited).

3. The fluorinated ether compound according to claim 1, wherein $R^{f1}$ is a group represented by the following formula (3-1), a group represented by the following formula (3-2), or a group represented by the following formula (3-3):

$$-R^F-O-CHFCF_2- \quad (3-1)$$

$$-R^F-CHFCF_2- \quad (3-2)$$

$$-R^F-C_zH_{2z}- \quad (3-3)$$

wherein $R^F$ is a single bond, a $C_{1-15}$ perfluoroalkylene group, or a $C_{2-15}$ perfluoroalkylene group having an etheric oxygen atom between carbon-carbon atoms; and z is an integer of from 1 to 4.

4. The fluorinated ether compound according to claim 1, which has a number average molecular weight of from 2,000 to 10,000.

5. A fluorinated ether composition comprising the fluorinated ether compound as defined in claim 1, and a fluorinated ether compound other than the fluorinated ether compound represented by the above formula (1).

6. The fluorinated ether composition according to claim 5, wherein the content of the fluorinated ether compound represented by the above formula (1) is at least 70 mass % in the fluorinated ether composition (100 mass %).

7. The fluorinated ether composition according to claim 5, wherein the fluorinated ether compound other than the fluorinated ether compound represented by the above formula (1) is a fluorinated ether compound represented by the following formula (2):

$$D^2-R^{f2}-O-CH_2-(C_pF_{2p}O)_q-C_dF_{2d}-CH_2-O-R^{f3}-D^3 \quad (2)$$

wherein each of $D^2$ and $D^3$ which are independent of each other, is $CF_3-$ or $CF_3-O-$; each of $R^{f2}$ and $R^{f3}$ which are independent of each other, is a $C_{1-20}$ fluoroalkylene group, or a $C_{2-20}$ fluoroalkylene group having an etheric oxygen atom between carbon-carbon atoms; d is an integer of from 1 to 5; p is an integer of from 1 to 6; q is an integer of from 1 to 200, provided that when q is 2 or more, $(C_pF_{2p}O)_q$ may be made of two or more types of $C_pF_{2p}O$ different in p.

8. The fluorinated ether composition according to claim 7, wherein the total content of the fluorinated ether compound represented by the above formula (1) and the fluorinated ether compound represented by the above formula (2) is at least 80 mass % in the fluorinated ether composition (100 mass %).

9. The fluorinated ether composition according to claim 5, wherein the fluorinated ether compound other than the fluorinated ether compound represented by the above formula (1) is a fluorinated ether compound represented by the following formula (6):

$$R^{F1}-O-(C_sF_{2s}O)_t-R^{F2} \quad (6)$$

wherein each of $R^{F1}$ and $R^{F2}$ which are independent of each other, is a $C_{1-6}$ perfluoroalkyl group; s is an integer of from 1 to 6; and t is an integer of from 1 to 200, provided that when t is 2 or more, $(C_sF_{2s}O)_t$ may be made of two or more types of $C_sF_{2s}O$ different in s.

10. A coating liquid comprising the fluorinated ether composition as defined in claim 5 and a medium.

11. The coating liquid according to claim 10, wherein the medium is at least one organic solvent selected from the group consisting of a fluorinated alkane, a fluorinated aromatic compound and a fluoro-alkyl ether.

12. A method for producing a substrate having a surface layer, which comprises applying the coating liquid as defined in claim 10, on a surface of a substrate, followed by drying.

13. A method for producing a substrate having a surface layer, which comprises vacuum vapor depositing the fluorinated ether composition as defined in claim 5, on a surface of a substrate.

14. A substrate having a surface layer which is formed of the fluorinated ether composition as defined in claim 5.

15. A touch panel having, on its input surface, a substrate having a surface layer which is formed of the fluorinated ether composition as defined in claim 5.

16. A coating liquid comprising the fluorinated ether compound as defined in claim 1 and a medium.

17. The coating liquid according to claim 16, wherein the medium is at least one organic solvent selected from the group consisting of a fluorinated alkane, a fluorinated aromatic compound and a fluoro-alkyl ether.

18. A method for producing a substrate having a surface layer, which comprises applying the coating liquid as defined in claim 16, on a surface of a substrate, followed by drying.

19. A method for producing a substrate having a surface layer, which comprises vacuum vapor depositing the fluorinated ether compound as defined in claim 1, on a surface of a substrate.

20. A substrate having a surface layer which is formed of the fluorinated ether compound as defined in claim 1.

21. A touch panel having, on its input surface, a substrate having a surface layer which is formed of the fluorinated ether compound as defined in claim 1.

* * * * *